United States Patent [19]

Gupta et al.

[11] Patent Number: 5,036,007
[45] Date of Patent: Jul. 30, 1991

[54] METHOD FOR REPRODUCING CONIFEROUS PLANTS BY SOMATIC EMBRYOGENESIS USING ABSCISIC ACID AND OSMOTIC POTENTIAL VARIATION

[75] Inventors: Pramod K. Gupta, Federal Way; Gerald S. Pullman, Renton, both of Wash.

[73] Assignee: Weyerhaeuser Company, Tacoma, Wash.

[21] Appl. No.: 499,151

[22] Filed: Mar. 26, 1990

Related U.S. Application Data

[63] Continuation-in-part of Ser. No. 321,035, Mar. 9, 1989, Pat. No. 4,957,866, and a continuation-in-part of Ser. No. 426,331, Oct. 23, 1989.

[51] Int. Cl.$^5$ .................... A01H 4/00; A01H 7/00; C12N 5/04
[52] U.S. Cl. .................... 435/240.45; 435/240.4; 435/240.46; 435/240.47; 435/240.49; 435/240.54; 435/172.1; 800/200; 800/DIG. 49; 800/DIG. 50; 800/DIG. 51
[58] Field of Search ........... 435/240.4, 240.45, 240.46, 435/240.47, 240.49, 240.54; 800/200

[56] References Cited

U.S. PATENT DOCUMENTS 4,217,730  8/1980  El-Nil .................... 47/58

OTHER PUBLICATIONS

Hakman et al., (1985), J. Plant Physiology, vol. 121, pp. 149–158.
Von Arnold et al., (1987), J. Plant Physiology, vol. 128, pp. 233–244.
Panott et al., (1988), In vitro Cellular & Developmental Biology, vol. 24, #8, pp. 817–820.
Fridborg et al., (1975), Physiol Plant, vol. 34, pp. 306–308.
Bu et al., (1988) ACTA Phytophysiol Sin 14(4), pp. 401–405.
Becwar, M. R. and R. P. Feirer, 1989, Factors Regulating Loblolly Pine *Pinus taeda* L.) Somatic Embryo Development, *Institute of Paper Chemistry Report*, Southern Forest Tree Improvement Conference, Raleigh, N.C., Jun. 1989.
Becwar, M. R., T. L. Noland, and S. R. Wann, 1987, A Method for Quantification of the Level of Somatic Embryogenesis Among Norway Spruce Callus Lines, *Plant Cell Reports* 6: 35–38.
Becwar, M. R., S. R. Wann, and R. Nagmani, 1988, A Survey of Initiation Frequency of Embryogenic Callus Among Ten Families of *Pinus taeda* (loblolly pine), *Abstracts*, 4th International Conifer Tissue Culture Work Group, Aug. 8–12, 1988, Saskatoon, Saskatchewan, Canada.
Boulay, M. P., P. K. Gupta, P. Krogstrup, and D. J. Durzan, 1988, Development of Somatic Embryos from Cell Suspension Cultures of Norway Spruce (*Picea abies* Karst.), *Plant Cell Reports* 7: 134–137.

(List continued on next page.)

*Primary Examiner*—Howard J. Locker
*Assistant Examiner*—Gary Benzion

[57] ABSTRACT

The invention is a method for developing tissue culture induced coniferous somatic proembryos into well developed cotyledonary embryos. The method comprises a multistage culturing process in which early stage proembryos are cultured on a late stage proembryo medium comprising a significantly higher osmotic potential along with abscisic acid and an absorbent material to gradually reduce the level of available abscisic acid over time. Culturing from this point continues in an embryo development medium having a high osmotic potential in which the osmotic potential is preferably raised during embryo development to a final level of about 450 mM/kg. Through this process the vigor and morphology of the embryos is improved and the tendency to germinate prematurely is significantly reduced. After a period of several weeks in culture somatic embryos having the appearance of zygotic embryos will have formed. These may be germinated before or after storage and transplanted to the soil for further growth.

26 Claims, 5 Drawing Sheets

OTHER PUBLICATIONS

Bourgkard, F. and J. M. Favre, 1988, Somatic Embryos from Callus of *Sequoia Sempervirens*, Plant Cell Reports 7: 445–448.

Buchheim, Julie A., Susan M. Colburn, and Jerome P. Ranch, 1989, Maturation of Soybean Somatic Embryos and the Transition to Plantlet Growth. *Plant Physiology* 89: 768–775.

Durzan, D. J. and P. K. Gupta, 1987, Somatic Embryogenesis and Polyembryogenesis in Douglas-Fir Cell Suspension Cultures, *Plant Science* 52: 229–235.

Finer, John J., Howard B. Kriebel, and Michael R. Becwar, 1989, Initiation of Embryogenic Callus and Suspension Cultures of Eastern White Pine (*Pinus strobus* L.), *Plant Cell Reports* 8: 203–206.

Gupta, Pramod K. and Don J. Durzan, 1985, Shoot Multiplication from Mature Trees of Douglas-Fir (*Pseudotsuga menziesii*) and Sugar Pine (*Pinus lambertiana*), *Plant Cell Reports* 4: 177–179.

1986a, Somatic Polyembryogenesis from Callus of Mature Sugar Pine Embryos, *Bio/Technology* 4: 643–645.

Gupta, Pramod and Don J. Durzan (cont.), 1986b, Plantlet Regeneration via Somatic Embryogenesis from Subcultured Callus of Mature Embryos of *Picea abies* (Norway Spruce), *In Vitro Cellular and Developmental Biology* 22: 685–688.

1987, Biotechnology of Somatic Polyembryogenesis and Plantlet Regeneration in Loblolly Pine, *Bio/Technology* 5: 147–151.

1988, Somatic Embryogenesis and Plant Regeneration from Suspension Cultures of *Picea glauca* (White Spruce), *Physiologia Plantarum* 72: 579–587.

Hakman, Inger, L. C. Fowke, Sara von Arnold, and Tage Eriksson, 1985, The Development of Somatic Embryos in Tissue Cultures Initiated from Immature Embryos of *Picea abies* (Norway Spruce), *Plant Science* 38: 33–35.

Johansson, Lars, 1983, Effects of Activated Charcoal in Anther Cultures, *Physiologia Plantarum* 59: 397–403.

Johansson, Lars, Barbro Andersson, and Tage Eriksson, 1982, Improvement of Anther Culture Technique: Activated Charcoal Bound in Agar Medium in Combination with Liquid Medium and Elevated $CO_2$ Concentration, *Physiologia Plantarum* 54: 24–30.

Lu, Chen-Yi, and Trevor A. Thorpe, 1987, Somatic Embryogenesis and Plantlet Regeneration in Cultured Immature Embryos of *Picea glauca*, *Journal of Plant Physiology* 128: 297–302.

Murashige, Toshio and Folke Skoog, 1962, A Revised Medium for Rapid Growth and Bioassays with Tobacco Tissue Cultures, *Physiologia Plantarum* 15: 473–493.

Nagmani, R. and J. M. Bonga, 1985, Embryogenesis in Subcultured Callus of *Larix decidua*, *Canadian Journal of Forest Research* 15: 1088–1901.

Nagmani, R. and M. R. Becwar, 1988, Factors Affecting Somatic Embryo Development in Loblolly Pine, *Abstracts*, 4th International Conifer Tissue Culture Work Group, Aug. 8–12, 1988, Saskatoon Saskatchewan, Canada.

Raghavan, V.N., 1987, *Experimental Embryogenesis*, p. 100, McMillan, New York.

Schuller, Astrid and Gerhard Reuther, 1989, Response of *Abies alba* Embryonal-Suspensor Mass to Various Carbohydrate Treatments, *Somatic Cell Genetics Working Party S2-04-07 and NATO Advanced Research Workshop on Woody Plant Biology*, Institute of Forest Genetics, Placerville, Calif., Oct. 15–19, 1989, (Abstract).

Singh, Hardev, 1978, "Embryo" in *Embryology of Gymnosperms*, Chapter 11, Gebruder Borntrager, Berlin.

Teasdale, Robert D., Pamela A. Dawson, and H. W. Woolhouse, 1986, Mineral Nutrient Requirements of a Loblolly Pine, (*Pinus taeda* Cell Suspension Culture, *Plant Physiology* 82: 942–945.

Von Arnold, Sara, 1987, Improved Efficiency of Somatic Embryogenesis in Mature Embryos of *Picea abies* (L.) Karst., *Journal of Plant Physiology* 128: 233–244.

Von Arnold, Sara and Inger Hakman, 1988, Regulation of Somatic Embryo Development in *Picea abies* by Abscisic Acid (ABA), *Journal of Plant Physiology* 132: 164–169.

Yeung, Edward C. and D. C. W. Brown, 1982, The Osmotic Enviornment of Developing Embryos of *Phaseolus vulgaris*, *Z. Pfanzenphysiol. Bd.*, 106 S.: 149–156.

Ziv, Meira and Geula Gadasi, 1986, Enhanced Embryogenesis and Plant Regeneration from Cucumber (*Cucumis sativus* L.) Callus by Activated Charcoal in Solid/Liquid Double-Layer Cultures, *Plant Science* 47: 115–122.

METHOD FOR REPRODUCING CONIFEROUS PLANTS BY SOMATIC EMBRYOGENESIS USING ABSCISIC ACID AND OSMOTIC POTENTIAL VARIATION

This application is a continuation-in-part of our earlier application Ser. No. 321,035, filed Mar. 9, 1989 now U.S. Pat. No. 4,957,866 and our pending Ser. No. 426,331, filed Oct. 23, 1989.

BACKGROUND OF THE INVENTION

The present invention is a method for reproducing coniferous plants by somatic embryogenesis using the techniques of plant tissue culture. It is especially suited for producing large clones of superior Douglas-fir selections useful for reforestation.

Loblolly pine (*Pinus taeda* L.), its closely related southern pines, and Douglas-fir (*Pseudotsuga menziesii* (Mirb.) Franco) are probably the most important commercial species of temperate North American timber trees. Since the early 1940s, when serious private reforestation efforts began, literally billions of one and two year old nursery-grown trees have been planted on cut-over or burned forest lands. For many years these seedling trees were grown using naturally produced seed from cones collected as a part time effort of individuals seeking to supplement their incomes. As early as 1957 forest genticists began to plant seed orchards using either seed or grafted scions obtained from superior trees. These trees were selected for such inheritable characteristics as rapid growth, straightness of bole, wood density, etc. Now in both the southern pine and Douglas-fir regions the bulk of the seed is produced from selected trees grown in seed orchards, some of them now second and third generation orchards.

Despite the fact that the orchards were stocked with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominately angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

Culture by organogenesis is tedious and expensive due to the large amount of delicate manual handling necessary. It was soon recognized that embryogenesis was potentially a much more desirable method from the standpoints of quantity of plantlets produced, cost, and potential genetic gain. Work on embryogenesis of forest species began in the late 1970s. U.S. Pat. No. 4,217,730 to El-Nil describes one early attempt at somatic embryogenesis of Douglas-fir. This approach was later set aside because advanced stage embryos and plantlets could not be readily obtained. However, other workers entered the field in increasing numbers and progress has been rapid even if it has not until the present time reached the commercial stage. A brief review of some of the most important work will follow. This is intended to be representative and is not fully inclusive of all the work in the field. Literature citations in the text are given in abbreviated form. Reference should be made to the bibliography at the end of the specification for full citations of the literature noted herein.

The natural embryogeny of gymnosperms is described in great detail by Singh (1978). Conifer-type embryogeny is one of four types noted for gymnosperms. This includes virtually all of the important forest species except Sequoia. Singh notes that the immature seeds typically contain more than one embryo. Most commonly this seems to occur when a single zygote forms multiple embryos, a phenomenon called "cleavage polyembryony". As the seed matures one embryo becomes dominant while the others are suppressed. The ability to form multiple embryos from a single zygote forms the basis for most of the present embryogenic processes for multiplying conifers. However, Douglas-fir is an exception. Most typically only a single embryo will be present throughout the formation and maturation of a seed. This may account for at least some of the difficulty experienced to date in multiplying Douglas-fir by somatic embryogenesis.

Bourgkard and Favre (1988) describe what is the apparently successful production of plantlets by somatic embryogenesis of *Sequoia sempervirens*. As a historic note, this was one of the first forest tree species successfully reproduced by organogenesis.

Hakman and her coworkers have concentrated on Norway spruce (*Picea abies*), apparently with some success. In a paper by Hakman, Fowke, von Arnold, and Eriksson (1985) the authors describe the production of "embryos" but not plantlets. Hakman and von Arnold (1985) do suggest that they have successfully obtained plantlets. This latter paper is interesting for its comments on the variability within the species and the poor success with many of the seed sources used for explants. The authors suggest that this variability may be due to the physiological condition of the source material. However, other workers have noted great differences in behavior between recognized genotypes of the species.

Nagmani and Bonga (1985) describe embryogenesis from megagametophytes of *Larix decidua* by tissue culture. The archegonia, proembryos, or embryos with their suspensors were removed prior to culture. Some of the resulting embryos produced in culture were stated to have further advanced to become plantlets established in soil. The ploidy of these plants was not investigated.

Successful production of small quantities of plantlets has now been reported for loblolly pine. Teasdale, Dawson, and Woolhouse (1986) showed the critically of proper mineral nutrients for cell suspension cultures of loblolly pine. The article by Becwar, Wann, and Nagmani (1988) is enlightening for the differences shown in performance between different families (or genotypes). Three families out of the ten tried accounted for most of their success. Even so, they appeared unable to grow cotyledonary embryos. A companion paper by Nagmani and Becwar (1988) showed development of *Pinus taeda* to the precotyledonary stage. In an earlier paper, Gupta and Durzan (1987) described their success in taking loblolly pine to the plantlet stage by embryogenesis. However, only one genotype was successfully taken to the plantlet stage and only one converted plant was produced. The authors note the need for "improved conversion rates" as well as other information before the process can be considered commercially practical.

Sugar pine (*Pinus lambertiana*) has also been cultured to the plantlet stage as reported by Gupta and Durzan (1986). The authors note a very low 1-2% conversion of embryos into plantlets.

The above researchers appear to be the only ones who have previously achieved success in producing Douglas-fir plantlets by embryogenesis (Durzan and Gupta 1987). Again, the success ratio appears to be very low and they have obtained only two converted plants from a single genotype.

In our earlier application, Ser. No. 321,035, filed Mar. 9, 1989, now U.S. Pat. No. 4,957,866 which is a parent to the present application, we described an improved method for reproducing coniferous species by somatic embryogenesis. An intermediate high osmoticant culture medium was used to generate strong late stage proembryos, prior to the development of cotyledonary embryos in a medium containing abscisic acid. The methods disclosed were of particular effectiveness in somatic polyembryogenesis of loblolly pine. In Ser. No. 426,331, filed Oct. 23, 1989, the other parent application to the present one, we disclosed the use of a combination of abscisic acid with activated charcoal in a cotyledonary embryo development medium. This improvement resulted in the development of more robust embryos with a much reduced tendency for precocious germination.

Activated charcoal has been widely used before in tissue culture media where it is believed to function as an adsorbent for toxic metabolic products and undesirable amounts of residual hormones. Abscisic acid has also been recognized as being a useful plant hormone in cultures inducing conifer embryogenis; e.g., Boulay, Gupta, Krogstrup, and Durzan (1988). The combination of these two materials has been used by a number of workers, generally with indifferent or negative results. Johansson, Andersson, and Ericksson (1982) cultured anthers of several ornamental plant species using a two phase liquid over solid medium in which the agarified solid phase contained activated charcoal. The charcoal appeared to be useful for absorbing small amounts endogenous abscisic acid. In a related paper Johansson (1983), tested the effects of charcoal as an adsorbent of materials inhibiting the initiation of embryogenesis. In a test intended as a model, he added exogenous ABA in amounts varying by orders of magnitude between $10^{-9}M$ and $10^{-3}M$ to media with and without activated charcoal in the solid portion of a two phase medium. His conclusion was that initiation was completely inhibited for all of the test species at ABA concentrations above $10^{-6}M$, when no charcoal was used, and $10^{-4}M$ when charcoal was present. Thus, charcoal was seen as an effective material for removing inhibitory amounts of ABA and other undesirable materials such as phenolics.

Ziv and Gadasi (1986) studied embryogenesis in several genotypes of cucumber (*Cucumis sativus* L.). They used liquid cultures as well as the two layer technique with activated charcoal in the solid layer of the medium and low (0.4 $\mu M$) levels of abscisic acid in the liquid layer. In the liquid cultures abscisic acid by itself only slightly improved embryo formation and was significantly more effective than the combination of abscisic acid with activated charcoal. Plantlet development in the liquid over solid cultures was slightly improved by the combination of the two materials.

Buchheim, Colburn, and Ranch (1989) suggest that exogenous abscisic acid and activated charcoal would probably not be a very useful combination of ingredients in a culture medium because of adsorption of the abscisic acid by the charcoal with subsequent loss of its biological effectiveness.

Since the importance of the osmotic environment within a developing seed is known (Yeung and Brown 1982), it has been assumed by others that the osmotic potential of the media during a culturing process could have an important effect (e.g., Raghavan 1987). Lu and Thorpe (1987), using white spruce (*Picea glauca*), noted that increasing the osmolarity of a medium and reducing the auxin concentration enhanced development and maturation of somatic embryos. They observed that more embryos developed on media containing 6% than on those with 9% sucrose and that similar results were obtained when sorbitol replaced 3% of the sucrose in the medium. Sorbitol is known to be only poorly metabolized so presumably its effect was osmotic rather than as a carbon source for the developing embryos. Quite in contrast to their findings, Hakman and von Arnold (1988), using the same species and a combination of abscisic acid and sucrose in a development medium, found a very sharp falloff in success in going from 3% to 4% sucrose.

Becwar and Feirer (1989) note work involving the transfer of a loblolly pine embryonal-suspensor mass to development media containing 10 $\mu M$ abscisic acid with 3-6% sucrose. However, they reported no details of their experimental protocol and only that the media "promoted embryo development". While a report (Becwar et al.) is noted as being in press it has apparently not yet been published.

Finer, Kreibel and Becwar (1989), studying eastern white pine (*Pinus strobus* L.), initiated and maintained cultures on media with a 3% sucrose level. Further embryo development was then attempted on a medium with 1-12% sucrose combined with a high concentration of abscisic acid and varying amounts of glutamine. Best results were found with 50 mM glutamine, 36 $\mu M$ abscisic acid, and 6% sucrose. However, the number of embryos formed under any of the conditions was not high and, as of the time of reporting, none had been successfully germinated and converted into plants.

Schuller and Reuther (1989), in the abstract of a paper, describe the study of several sugars and soluble starch as carbohydrate sources for the culture of *Abies alba*. They note that development was obtained only on a medium using soluble starch and lactose. No details were given and apparently no somatic embryos were developed to the cotyledonary stage.

Von Arnold (1987) investigated carbohydrate level of the initiation medium for Norway spruce. Sucrose was varied between about 1-3% with successful initiation being obtained at the higher level on half strength medium. By replacing a portion of the sucrose with sorbitol she showed that the poorer results on full strength medium were not due to increased osmotic pressure.

Von Arnold and Hakman (1988) took a Norway spruce embryogenic callus and transferred it to a modified intermediate medium prior to full embryo development. The intermediate medium contained abscisic acid and from 1–3% sucrose. The higher sucrose levels, along with the abscisic acid, resulted in increased frequency of advanced stage proembryo development.

The potential for achieving genetic gain using somatic embryogenesis is recognized as being very great. However, the problems to date have been so overwhelming that commercial application has seemed reasonably close at hand only for Norway spruce and, to a lesser extent, loblolly pine using the methods described in our parent applications. Successful embryogenesis of Douglas-fir has been much more elusive. Until the present time, while some converted trees have been obtained, the percentage of success has been far below that of the two previously named species. Possible commercial production of Douglas-fir replanting stock by embryogenesis has remained no more than a fond hope in the minds of the people working in the field.

SUMMARY OF THE INVENTION

The present invention is a method of reproducing selected plants by somatic embryogenesis using tissue culture techniques. The method is particularly suitable for reproducing woody gymnosperms of the order Coniferales. It is especially well suited for generating large clones of superior forest trees for reforestation, including, species within the families Pinaceae, Cupressaceae, and Taxodiaceae. Most or all species within the genera Abies, Pinus, Picea, Tsuga, Pseudotsuga, Thuja, Juniperis, Larix, and Sequoia are believed to be well suited for multiplication by the present method. The present method is most especially useful for reproducing Douglas-fir (*Pseudotsuga menziesii* (Mirb.) Franco.)

The method is particularly advantageous in that it enables greater quantities and more robust somatic embryos to be produced. This results in higher numbers of embryos that can be successfully converted into plants growing in soil. Costs per plant can be significantly reduced over prior known tissue culture methods. In addition, use of the method generates embryos that can be retained for extended periods of time in cold storage without transferring them from a development medium.

A number of terms are known to have differing meanings when used in the literature. The following definitions are believed to be the ones most generally used in the field of botany and are consistent with the usage of the terms in the present specification.

"Auxins" are plant growth hormones that promote cell division and growth.

"Cytokinins" are plant growth hormones that affect the organization of dividing cells.

"Callus" is generally considered to be a growth of unorganized and either unconnected or loosely connected plant cells generally produced from culturing an explant.

"Embryogenic callus" is a translucent white mucilagenous mass that contains early stage proembryos attached to suspensors. This is also referred to as an "embryonal-suspensor mass" or "ESM" by some investigators.

A "proembryo" is a cell or group of cells having the potential to become a plant but lacking defined meristematic organ primordia.

An "early stage proembryo" is a mass generally of 1–10 cells with dense cytoplasm and large nuclei that have the potential of forming a plant. The early stage proembryo is normally found as a head associated at the end of a long thin-walled suspensor cell (FIG. 1).

A "late stage proembryo" is a proembryo with a smooth embryonal head of at least about 100 cells associated with multiple suspensor cells. The late stage proembryo is a very robust advanced proembryo (FIG. 2).

A "cotyledonary embryo", sometimes simply referred to as an "embryo", has a well defined elongated bipolar structure with latent meristem with cotyledonary primordia at one end and a potential radicle at the opposite end. The cotyledonary structure frequently appears as a small "crown" at one end of the embryo (FIGS. 3 and 9). A cotyledonary somatic embryo is analogous to a developed zygotic embryo.

An "explant" is a piece of tissue taken from a donor plant for culturing.

A "meristem" or "meristematic center" is a group of tissue forming cells capable of further development into plant organs; e.g., shoots and roots.

An "osmoticant" or "osmoticum" is a chemical material used for controlling the osmotic potential of a solution. In the present context the solution would be a culture medium.

A "plantlet" is a plant asexually reproduced by tissue culture (FIG. 4).

A "converted embryo" is an embryo that has germinated and been established as a plant growing in soil "Somatic embryogenesis" is the process using tissue culture techniques for generating multiple embryos from an explant. The embryos from a given tissue source are presumed to be genetically identical.

The present method comprises a multistage culturing process. A suitable explant is first placed on an induction or initiation culture medium. This usually will contain relatively high quantities of growth hormones including at least one auxin and frequently one or more cytokinins. However, growth hormones at this initial stage are not always necessary or desirable for induction of early stage proembryos. A number of sources of explants may ultimately prove to be satisfactory for culturing. These include, but are not limited to, tissue from cotyledons, hypocotyls, epicotyls, buds, meristematic centers for buds or roots, and seed embryos. Zygotic embryos removed from seeds are presently preferred. In particular, for species which in the past have proved to be very difficult or impossible to propagate by somatic embryogenesis, the embryos from immature seeds may be preferred. In the case of Douglas-fir, an embryo selected between the time that an apical dome begins to form but before the first appearance of cotyledon primordia appears to be optimum.

The first stage or induction medium will normally be one of those well known from past work which contain a balanced concentration of inorganic salts and organic nutrient materials, with plant growth hormones included as noted above. Auxins are normally present in concentrations which may initially be as high as about 600 $\mu$M/L, more typically not exxeeding about 500 $\mu$M/L. Cytokinins, if present, may initially be as high as 500 $\mu$M/L. The plant growth hormones may include at least one auxin and one cytokinin in a combined initial concentration not exceeding about 1100 μM/L, more typically not exceeding about 900 μM/L. The particular auxins and cytokinins used and their exact concentrations, or whether they are used at all, will depend somewhat on the species being cultured and even on the particular genotype within that species. This is something that cannot be easily predicted but can be readily determined experimentally. These very high levels of growth hormones assume the presence in the medium of an adsorbent material, such as activated charcoal. Where charcoal is not present the levels of growth hormones would normally be much lower than those just noted.

Culturing during this stage may be carried out in the dark, under very low light conditions, or in full light until an embryogenic mass forms. Lighting conditions will depend in large part on the composition of the particular medium selected. This embryogenic mass has been described by various other names by researchers who have reported it in the past; e.g., embryogenic callus (Hakman and von Arnold 1985) or embryonal-suspensor mass (Durzan and Gupta 1987). It has the appearance of a whitish, translucent, mucilagenous mass containing early stage proembryos which are readily apparent by low power light microscopy. In the case of Douglas-fir the presence of activated charcoal or a similar adsorbent in the initiation medium appears to be quite advantageous. It was noted earlier that Douglas-fir does not experience polyembryony as do most other coniferous species. The reasons for this are not well understood but one hypothesis suggests that Douglas-fir seeds contain a high endogenous level of abscisic acid which prevents polyembryony. Activated charcoal in the initiation medium may remove this endogenous ABA, as well as other undesirable metabolic byproducts, to allow polyembryony to occur in vitro. Because the charcoal will also gradually remove growth hormones over time the initial concentrations of these materials are necessarily higher than might otherwise be the case. The preferred induction medium for Douglas-fir will preferably contain an auxin or auxins in amounts of about 400–600 μM/L and a cytokinin or cytokinins in the amount of about 240–500 μM/L.

Early stage proembryos from the first culture may be directly transferred to a late proembryo development culture medium having significantly reduced plant growth hormones and, for some species, a higher concentration of osmoticants. However, they are preferably first subcultured in a maintenance medium of similar or slightly higher osmotic potential than the induction medium for multiplication. This multiplication medium will also usually have the concentration of plant hormones significantly reduced below that of the induction medium. By "significantly reduced" is meant lowered by a factor which may typically be one whole order of magnitude. In the case of Douglas-fir it may be two full orders of magnitude. No hormone adsorbent is usually necessary or desirable at this time. The osmotic potential of the induction and maintenance medium will most often not exceed about 160 mM/kg.

The composition and use of the late proembryo development culture medium is important to the success of the present process. It differs from the induction medium by having a similar level of plant growth hormones to those present in the maintenance and multiplication medium. However, for many species such as Pinus taeda and Pseudotsuga menziesii, the late proembryo development media should have a concentration of osmoticants that is significantly raised above that of the induction or multiplication media. The optimum osmoticant levels at each stage will usually differ for each species and often for individual genotypes within a species. For loblolly pine the osmotic level should typically be of the magnitude of at least 200 mM/kg and preferably about 240 mM/kg or even higher. However, lower levels of about 170 mM/kg minimum will suffice for most genotypes of Douglas-fir. The key advantage of this osmotic "pulse" is that proembryo quality and/or size can be significantly improved. Some species such as Picea abies, which are relatively easy to reproduce, may not generally require this raised osmotic level, or it may only be necessary for some genotypes. In these cases late proembryo development may usually be achieved without a change in medium composition from the maintenance and multiplication medium.

Incubation at this stage is usually carried out in the dark or in greatly reduced light until robust late stage proembryos have formed. These may then be transferred to an embryo development medium which preferably lacks auxins and cytokinins entirely.

Many investigators refer to cotyledonary embryo development simply as a "development" stage and that usage will be understood herein unless the word "development" is otherwise qualified.

Douglas-fir requires an intermediate step between the late proembryo development stage and cotyledonary embryo development stage which is not necessary for other species. The proembryos tend to form in tight clumps or clusters (FIG. 6) which must first be singulated before going to the development stage. This singulation is carried out in a liquid shake culture which lacks auxins and cytokinins but has exogenous abscisic acid as a necessary new hormone. The level of osmotic potential is also reduced from that of the late stage proembryo development medium. ABA will typically be within the range of 5–15 ppm (20–60 μM/L) with osmotic potential levels in the range of 130–140 mM/kg. It is most desirable when transfers to fresh media are made that the initial ABA level of the fresh medium should not be higher than the final level of the medium at the end of the preceeding culture period. This will ensure a continuously dropping level of ABA during the singulation period. The singulated late stage proembryos (FIG. 7) can then be transferred to a cotyledonary embryo development medium. If the embryos are not singulated they will develop into a tight clump of cotyledonary embryos which cannot be readily separated and are useless for further germination (FIG. 8.).

Especially when Douglas-fir is being cultured, the osmotic potential of the development medium should be sharply raised above that of any of the preceeding media. Initial levels may be in the 300–350 mM/kg range but these should be increased to levels of at least about 400 mM/kg as development proceeds. If development is started at levels around 300–350 mM/kg, the osmotic level may be increased during development by a complete medium change, a partial change in which some old medium is replaced, or by adding an appropriate form, such as a solution, of osmoticants to the medium without replacement of any of the original medium. Any of these changes may be considered a transfer to a "new" medium. It is preferred that the osmotic levels at the end of the development period should be at least about 450 mM/kg although with some genotypes lower levels are acceptable. These higher levels tend to prevent deterioration and callusing of the embryos.

Osmotic potential is best controlled by a combination of osmoticants. One of these should be a readily metabolized carbohydrate energy source, preferably a sugar such as sucrose, glucose, fructose, maltose, or galactose. Sucrose is a preferred ingredient but should be present in amounts only in the range of 2-3%. The other is a poorly metabolized osmoticant of which sorbitol, lactose, or a polyalkylene glycol would be examples. In a solid development medium, a combination of sorbitol, lactose and polyethylene glycol has proved very effective. Polyethylene glycol alone, in concentrations of 20-30% of the medium, has worked very well in liquid development media. While the salts and organic components of the medium make a small contribution to the osmolality, the osmotic potential is primarily controlled by the energy-providing sugar and the other osmoticants. It is within the scope of the invention to use one combination of osmoticants at the beginning of development and transfer to a medium having a different combination at some point during the development stage.

For many species a supply of exogenous abscisic acid is a desirable component in the development medium. This is always used in combination with an adsorbent, such as activated charcoal. The adsorbent should be present in a sufficient amount and form to slowly reduce the abscisic acid and remove metabolic waste products. It should not be present in such a high concentration as to deplete the abscisic acid in a very short time; e.g., in a matter of days. The combination of abscisic acid with the adsorbent will usually require a higher initial concentration of abscisic acid than would be the case if no adsorbent was present in the medium. In the particular case of Douglas-fir, and perhaps other species as well, the level of exogenous abscisic acid should be generally continuously lowered over time from the 5-15 ppm normally found necessary at the beginning of the singulation step to a level perhaps of about 1-2 ppm, or even to zero, at the end of the development stage. Accurate measurements of abscisic acid present in the development system have not yet been made due to the extreme difficulties of analyzing the medium.

In some cases when Douglas-fir is being cultured, sufficient abscisic acid will be carried over with the medium associated with the embryos from the singulation step so that no additional ABA is needed in the development medium. In other cases, the level of endogenous ABA after singulation is sufficiently high so that no exogenous ABA need be present at all. The terms "sufficient" or "having an adequate supply of" should be considered broad enough to encompass all of these situations. A small amount of activated charcoal, usually in the range of about 0.02-0.04% still appears to be necessary in the development medium to effect the continuing reduction in ABA that began with the singulation treatment. Reduction of ABA to low levels at the end of the development stage seems to help continue late embryo development and maturation and also reduces the tendency of precocious germination of the embryos.

Following embryo development the embryos (FIG. 9) may be placed directly on a germination medium for conversion into plantlets. Alternatively, they may be converted into artificial seeds by any of a number of published processes.

An advantage of the present process was the discovery that the more robust somatic embryos produced by the use of the abscisic acid-adsorbent combination could be readily stored for extended periods of time. Several genotypes of at least two coniferous species (*Pinus taeda* and *Picea abies*) have now been stored without loss of vitality for three months at 4°-5° C. without removing them from the development medium. *Pseudotsuga menziesii* has been stored for over one month. This has not been believed possible with any degree of success before the present invention.

The germination medium has no hormones, a lowered organic nitrogen content, and a reduced level of osmoticants. After a sufficient time in darkness followed by light, or a 16 hour light and 8 hour dark photoperiod, the cotyledonary embryos will have developed into plantlets. Douglas-fir does not require an initial dark period although a one week dark period is useful for Norway spruce. The time period for germination will be about 1-2 months. The resulting plantlets will have a well developed radicle and cotyledonary structure with a growing epicotyl and are ready for planting in soil.

The present invention is most particularly concerned with the composition of the cotyledonary embryo development media and method of its use. For Douglas-fir, it has been found that a very high osmotic level in combination with a diminishing level of exogenous abscisic acid is essential. This combination gives greatly improved numbers and quality of somatic embryos that are not subject to precocious germination.

It is an object of the present invention to produce coniferous plantlets by somatic embryogenesis.

It is another object to produce a large clone of a genetically selected forest species for reforestation using the methods of somatic embryogenesis and plant tissue culture.

It is a further object to provide a method of somatic embryogenesis that will dependably and consistently provide coniferous plantlets in large quantities.

It is yet another object to provide a method of somatic embryogenesis that can dependably and consistently reproduce large clones of selected individuals of forest species that heretofore have not been successfully reproduced by this method.

It is still a further object to provide a method whereby superior genotypes of coniferous trees can be multiplied by tissue culture in the large quantities needed for reforestation.

It is also an object to provide a method that will produce somatic embryos in large quantities with improved robust morphology for conversion into plantlets.

It is a particular object to provide a method and suitable culture media for somatic embryogenesis of Douglas-fir that produces robust somatic embryos with a high percentage of conversion to plants growing in soil.

It still another object to provide a method that generates robust somatic embryos capable of withstanding extended periods of cold storage.

These and many other objects will become readily apparent to those skilled in the art by reading the following detailed description, taken in conjunction with the drawings.

BRIEF DESCRIPTION OF THE DRAWINGS

The figures show various stages of plant embryogenesis in which.

DETAILED DESCRIPTION OF THE PREFERRED EMBODIMENTS

Figure 1:
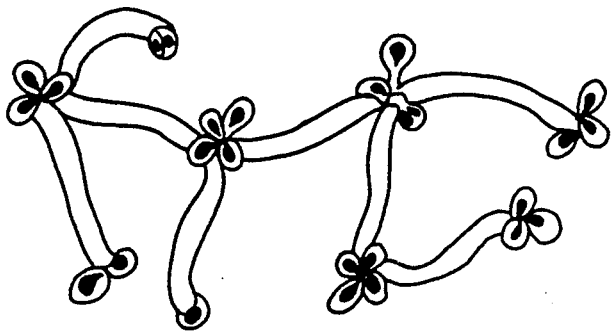
FIG. 1 shows early stage proembryos.

The process of the present invention is not limited to any single culture medium or to the use of specific growth hormones. Any of a number of well known media, such as that of Murashige and Skoog (1962), may be used. However, the present inventors have found the basal medium described in Table 1 to give excellent results, particularly when used for culturing loblolly pine (Pinus taeda). The basal medium is modified for each of the various culturing stages as shown in Table 2. Similar media particularly preferred for Norway spruce (Picea abies) are given in Tables 4 and 5.

TABLE 1

Pinus Taeda Basal Medium (Modified ½ P6 Basal Salts*)

| Constituent | Concentration, mg/L |
| --- | --- |
| $NH_4NO_3$ | 603.8 |
| $KNO_3$ | 909.9 |
| $KH_2PO_4$ | 136.1 |
| $Ca(NO_3)_2 \cdot 4H_2O$ | 236.2 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 6.95 |
| $Na_2EDTA$ | 9.33 |
| Sucrose | 30,000. |
| myo-Inositol | 1,000. |
| Casamino acids | 500.0 |
| L-Glutamine | 1000.0 |
| Thiamine.HCl | 1.00 |
| Pyridoxine.HCl | 0.50 |
| Nicotinic acid | 0.50 |
| Glycine | 2.00 |
| Agar+ | 6,000. |
| pH adjusted to 5.7 | |

*According to Teasdale, Dawson, and Woolhouse (1988) as modified
+Used if a solid medium is desired

TABLE 2

Composition of Media for Different Stage Treatments $BM_1$—Induction Medium
    BM + 2,4-D (50 μM) + KIN (20 μM) + BAP (20 μM)
$BM_2$—Maintenance and Multiplication Medium
    BM + 2,4-D (5 μM) + KIN (2 μM) + BAP (2 μM)
$BM_3$—Late Proembryo Development Medium
    $BM_2$ + 9000 mg/L myo-inositol
$BM_4$—Embryo Development Medium
    BM + 4.0 to 8.0 mg/L abscisic acid
$BM_5$—Germination Medium
    BM modified by reducing sucrose to 20,000 mg/L,
    myo-inositol to 100.0 mg/L, glutamine to 200.0 mg/L, and

TABLE 2-continued

Composition of Media for Different Stage Treatments casamino acids to 0.0 mg/L

A number of abbreviations are used in the following text. These are in common use in the field of tissue culture.

BAP—$N^6$-benzylaminopurine (or $N^6$-benzyladenine), a cytokinin

KIN—kinetin (6-furfurylaminopurine), also a cytokinin 2,4-D—2,4-dichlorophenoxyacetic acid, an auxin.

NAA—2-Naphthylacetic acid (Naphthalene-2-acetic acid)

ABA—Abscisic acid

It will be understood by those skilled in the art that other plant growth hormones can be substituted for those just noted. As examples, IAA (indole-3-acetic acid), IBA (indole-3-butyric acid), and NAA (naphthalene-2-acetic acid) are effective auxins and 2-IP ($N^6$-isopentenylaminopurine) and zeatin are frequently used as cytokinins.

As an aid in comparing the present work with other published data, the following table of conversions from weight to molar concentrations might be useful.

| | 1 μM/L | 1 mg/L |
| --- | --- | --- |
| BAP | 0.225 mg/L | 4.44 μM/L |
| KIN | 0.215 | 4.65 |
| 2,4-D | 0.221 | 4.52 |
| NAA | 0.816 | 5.38 |
| ABA | 0.264 | 3.78 |

In one of the parents of the present application, Ser. No. 321,035, we pointed out the importance of the control of osmotic potential of the media used in the various culturing stages. A large group of chemical materials are suitable as osmoticants. In general these are highly water soluble polyhydroxylated molecules that include either simple or complex sugars, hexitols, and cyclitols. The cyclitols are normally six carbon ring compounds that are hexahydroxylated. The most readily available cyclitol is myo-inositol but any of the other eight stereo-isomeric forms, such as scyllo-inositol are believed to be quite suitable. Among the sugars, sucrose and glucose are known to be very effective but many others should prove to be equally useful. Sorbitol (D-glucitol), D-mannitol, and galactitol (dulcitol) are straight chain sugar alcohols suitable as osmoticants. Lactose is a sugar effective as an osmoticant. Other materials suitable as osmoticants may include glycol ethers such as poly(ethylene glycol) and poly(propylene glycol) and their respective monomers.

LOBLOLLY PINE CULTURE

EXAMPLE 1

The following schedule of treatments has been very successfully used for the growth of plantlets by somatic embryogenesis of loblolly pine (Pinus taeda). Explants were immature embryos dissected from seeds 4 to 5 weeks after fertilization. Seeds were obtained from cones supplied by a Weyerhaeuser Company seed orchard located at Washington, N.C. The cones were stored at 4° C. until used. Immediately before removal of the immature embryos the seeds were sterilized using a modified method of Gupta and Durzan (1985).

Briefly, this involves an initial washing and detergent treatment followed by a first sterilization in 30% $H_2O_2$ and a second in diluted 10% v/v household bleach. The additional $HgCl_2$ treatment used by Gupta and Durzan was not found to be necessary to ensure sterility. The explants were thoroughly washed with sterile distilled water after each treatment.

Stage I—Induction. Sterile dissected embryos were placed on a solid $BM_1$ culture medium and held in an environment at 22°–25° C. with a 24 hour dark photoperiod for a time of 3–5 weeks. The length of time depended on the particular genotype being cultured. At the end of this time a white mucilagenous mass had formed in association with the original explants. This appears to be identical with that described by Gupta and Durzan (1987). Microscopic examination revealed numerous early stage proembryos associated with the mass. These are generally characterized as having a long thin-walled suspensor associated with a small head generally having less than 10 individual cells, each with dense cytoplasm and large nuclei. Early proembryos are illustrated in FIG. 1.

Osmolality of the induction medium may in some instances be as high as 200 mM/kg. Normally it will be below 175 mM/kg and, more typically, about 160 mM/kg or even lower. The osmolality of the medium described above was 158 mM/kg.

Stage II—Maintenance and Multiplication. Early stage proembryos removed from the masses generated in the induction stage were placed on a $BM_2$ medium. This differs from the induction medium in that the growth hormones (both auxins and cytokinins) were reduced by a full order of magnitude. The temperature and photoperiod were again 22°–25° C. with 24 hours in the dark. Osmolality of this medium will typically be similar or identical to that of the induction medium. In the present example it was identical. Proembryos developed in this stage were similar in appearance to those from Stage 1 and were subcultured every 12–15 days on $BM_2$ medium.

Figure 2:
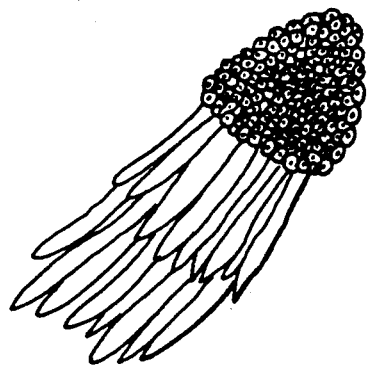
FIG. 2 shows late stage proembryos.

Stage III—Late Stage Proembryo Development. Early stage proembryos from either Stage I or Stage II, preferably the latter, were placed on a $BM_3$ solid medium. This medium has the same growth hormone concentration as $BM_2$, however, the osmoticant was raised to a much higher concentration. In this case the osmoticant, myo-inositol, was at a concentration of 10,000 mg/L or 1% on a w/v basis. Osmotic potential was measured as 240 mM/kg. Temperature and photoperiod were the same as for Stages I and II. After 3 or 4 subcultures of about 12–15 days each, very robust late stage proembryos had formed. These are characterized by smooth embryonal heads generally having in the neighborhood of over 100 individual cells with multiple suspensors, as exemplified in FIG. 2. Osmotic potential of the late proembryo development medium should usually fall within the range of about 200–400 mM/kg for *Pinus taeda*. Most typically it should be in the neighborhood of about 1.5 times higher than that of the induction or multipliction media. As was noted earlier, the requirements for elevation of osmotic potential at this stage will vary for different species.

Alternatively, the Stage II and/or Stage III proembryos could be cultured for late proembryo development in suspension in a liquid medium of similar composition to $BM_3$ but lacking the agar. In this case subcultures could be made every 7–8 days.

It is preferred that early stage proembryos brought into Stage III culture should have a Stage II subculturing for rapid multiplication of the particular clone. However, on occasions where time may be of greater importance than quantity, early stage proembryos from Stage I may be taken directly into Stage III.

Stage IV—Embryo Development. The late stage proembryos from Stage III culture were transferred to a solid $BM_4$ medium. This medium either lacks growth hormones entirely or has them present only at very low levels and has the same lower level of osmoticants as Stages I and II. However, abscisic acid (5-(1-hydroxy-2,6,6-trimethyl-4-oxo-2-cyclohexen-1-yl)-3-methyl-2,4-pentadienoic acid) had been included here as a necessary material for further development. A critical aspect of the present invention is the further inclusion of an adsorbent material in this medium. The adsorbent may be chosen from a number of chemical materials having extremely high surface area and/or controlled pore size such as activated charcoal, soluble and insoluble forms of poly(vinyl pyrrolidone), activated alumina, silica gel, molecular sieves, etc. The adsorbent will normally be present in a concentration of about 0.1–5 g/L, more generally about 0.25–2.5 g/L. The contribution of the adsorbent appears to be complex and is not well understood. Adsorbent materials, especially activated charcoal, have been widely used in the past in various culture media. However, the particular combination of activated charcoal with relatively large amounts of abscisic acid in a late stage somatic embryo development medium is believed to be entirely new. The prevailing wisdom found in the literature clearly teaches away from use of this combination, especially at this point in the process.

Figure 3:
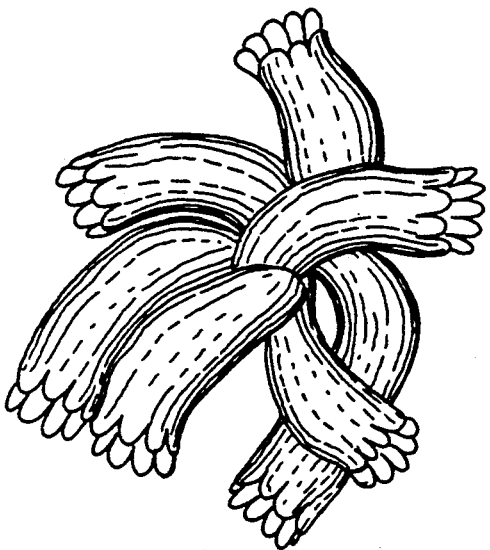
FIG. 3 depicts cotyledonary stage embryos.

The osmotic potential of this medium will generally be no greater than about 175 mM/kg. In the present case it was measured as 168 mM/kg. As before, development was carried out in complete darkness at a temperature of 22°–25° C. Development time was 4–6 weeks after which elongated cotyledonary embryos 4–5 mm long were present. These appeared as represented in FIG. 3.

Figure 4:
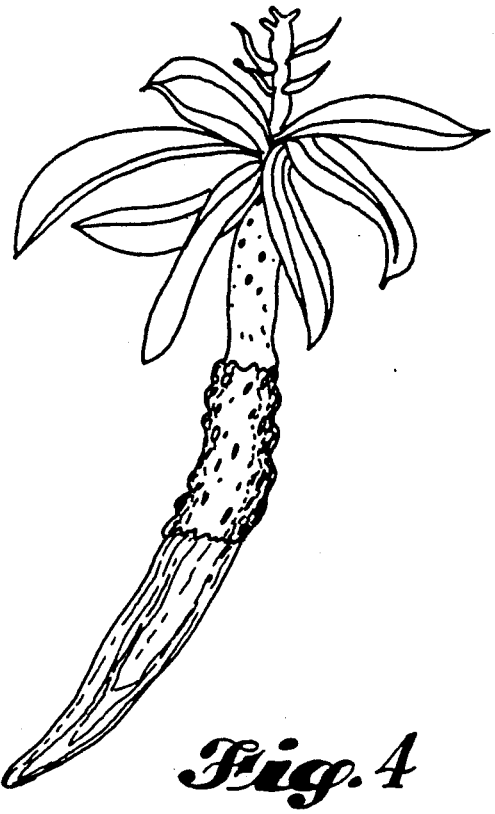
FIG. 4 shows a plantlet ready for transfer to soil.

Stage V—Germination. Cotyledonary embryos from Stage IV were placed on solid $BM_5$ medium for germination. This is a basal medium lacking growth hormones which has been modified by reducing sucrose, myo-inositol and organic nitrogen. After about 6–8 weeks under environmental conditions of 23°–25° C. and a 16 hour light/8 hour dark photoperiod the resulting plantlets were approximately 20 mm in length and had a well developed radicle and hypocotyl and green cotyledonary structure and epicotyl. The young plantlets are shown in FIG. 4.

Because of the reduced carbohydrate concentration, the osmotic potential of the germination medium is further reduced below that of the development medium. It will normally be below about 150 mM/kg and was, in the present example, about 100 mM/kg.

Stage VI—Plant growth. Plantlets from Stage V were removed from the culture medium and planted in a soil comprising equal parts of peat and fine perlite.

To the present time, three distinct genotypes of *Pinus taeda* have been successfully cultured through Stage V. Some of the plantlets have already been successfully transferred to soil and these are growing with good vigor. Two additional genotypes are being multiplied in Stage II prior to Stage III treatment. In work that preceeded that just described, all five genotypes when cultured without the Stage III high osmoticant treatment ultimately browned and died in Stage IV. Stated differently, the method failed completely when early stage *Pinus taeda* proembryos from Stage II were taken directly into Stage IV, as is taught in the prior art.

While inorganic salts and pure simple organic chemicals generally behave similarly in culture media regardless of supplier, there are occasions when this is not the case for the more complex materials. Without intending endorsement of any product over available alternatives, chemicals from the following suppliers were used throughout the experiments to be described in the examples. Agar was obtained from Difco Laboratories, Detroit, Mich. Where specified as "tissue culture agar" the supplier was Hazleton Biologics, Inc., Lenexa, Kans. Casamino acids, a casein hydrolysate, was also supplied by Difco Laboratories. Activated charcoal was obtained from Sigma Chemical Company, St. Louis, Miss., as their grade NuC-4386.

EXAMPLE 2

The combination of ABA and activated charcoal in the Embryo Development Medium has proved to be very effective not only with *Pinus taeda* but with other important conifer species such as *Picea abies* and *Pseudotsuga menziesii*. In the following experiments the Loblolly Pine Basal Media of Tables 1 and 2 were used. In the Embryo Development Medium the ABA was adjusted as described in Table 3 and activated charcoal was included in a concentration of 2.0 g/L. All of the ingredients except the abscisic acid were combined, autoclaved, and cooled to 50°-60° C. A filter sterilized solution of ABA was then added and mixed. After 10 minutes the medium was poured into petri dishes.

Late stage proembryo cells of two loblolly pine genotypes, grown as described in the first example, were settled from a suspension culture, the supernatant liquid poured off, and 1-1.5 mL of the settled cells were plated on the solid Embryo Development Medium in 5 cm dishes. These cultures were incubated in the dark at about 22° C. for six weeks. Control cultures having 2 and 4 mg/L ABA without activated charcoal were also prepared. The following results were obtained.

TABLE 3

| Medium Composition | | Embryos Produced | |
|---|---|---|---|
| ABA, mg/L | Activated Charcoal, g/L | Genotype A | Genotype B |
| 2.0 | 0.0 | 2.5 | — |
| 4.0 | 0.0 | 5.5 | — |
| 20.0 | 2.0 | 0 | 0 |
| 40.0 | 2.0 | 2 | 2 |
| 60.0 | 2.0 | 4 | 3 |
| 80.0 | 2.0 | 10 | 4.5 |
| 100.0 | 2.0 | 8.5 | 2 |

The embryos produced on the charcoal containing media were of better morphology with a well developed cotyledonary structure but without evidence of germinating precociously when compared to those grown without activated charcoal in the medium. The media described here are not represented as being optimized for the species or any genotype.

NORWAY SPRUCE CULTURE

EXAMPLE 3

Some coniferous species are relatively easier to propagate by somatic embryogenesis than others. Coastal redwood, *Sequoia sempervirens*, is considered be be a relatively easy species while Norway spruce, *Picea abies*, is usually thought to be of only moderate difficulty. Most members of the genus Pinus as well as Douglas-fir, *Pseudotsuga menziesii*, are regarded as very difficult. This has posed a major challenge to researchers since the latter two genera include a major percentage of the worlds most economically important timber species. Even though past researchers have reported success with somatic embryogenesis of several pines and of Douglas-fir, others in the field have frequently not been able to duplicate the work of these competent investigators. There are probably several reasons for this. Most certainly, one of them is over optimism on the part of researchers who have achieved and reported early stage embryogenesis or embryo-like structures but who later have not been able to succeed in producing significant numbers of cotyledonary embryos or plantlets. Another is the great differences in performance between different genotypes within a given species. *Picea abies* is a case in point. As noted earlier it is usually regarded as a species of only moderate difficulty to reproduce by somatic embryogenesis using present state-of-the-art technology. However, there are some genotypes of *Picea abies* that haven proven intractable to all previous efforts. Most researchers have limited themselves to working with only one or two genotypes that are known from past experience to give good results.

Figure 5:
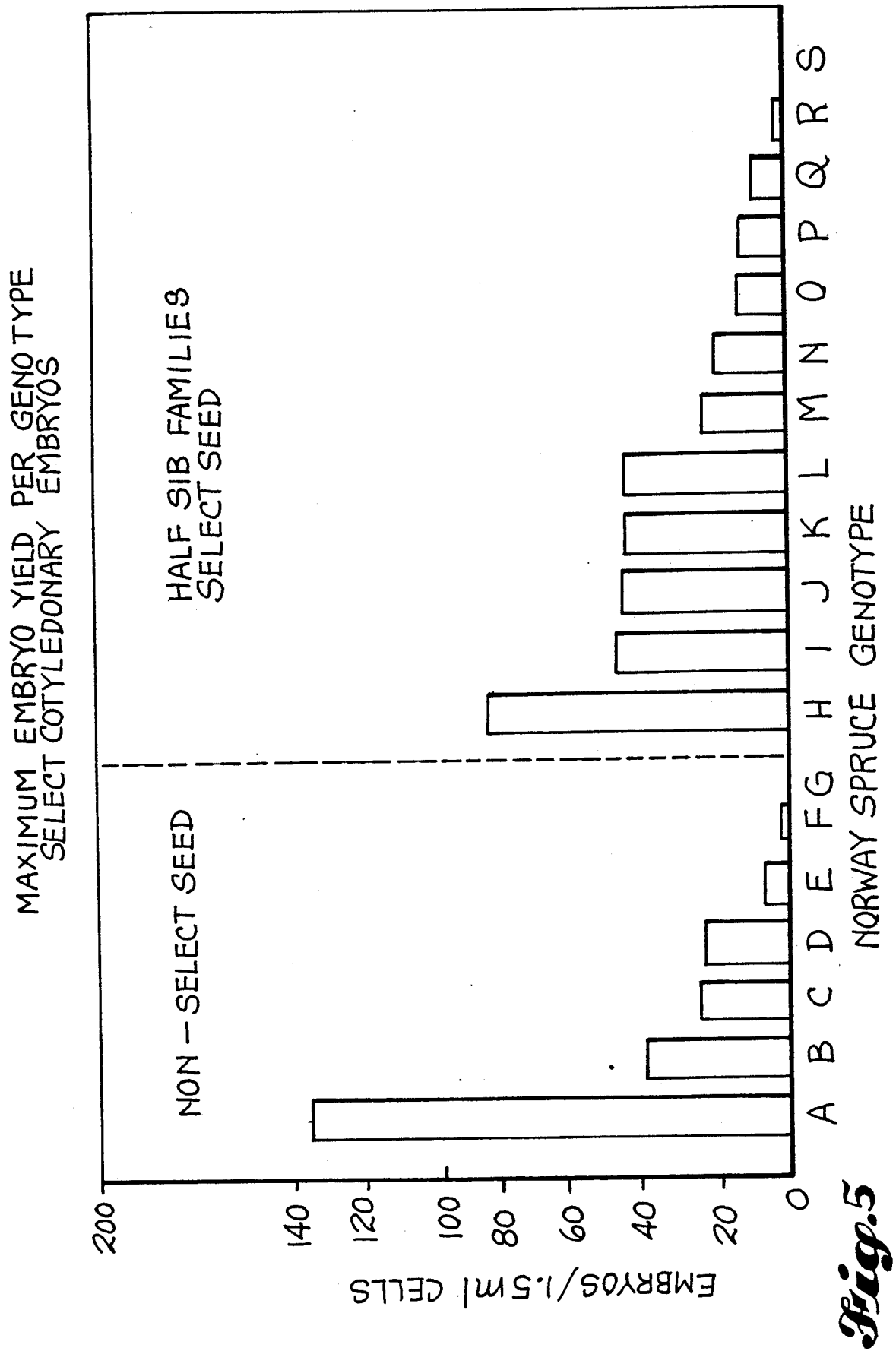
FIG. 5 shows the variation in behavior in tissue culture of various genotypes of a single coniferous species.

Our method has resulted in successful production of late stage proembryos and cotyledonary embryos on 23 of the 26 genotypes of *Picea abies* that have been investigated to date. This sample includes a considerable number of previously intractable genotypes. FIG. 5 shows the maximum yield of embryos per culture plate for 19 genotypes grown on the same nonoptimized culture (Medium No. 2 as described in Example 6). Seven of these are from non-select wild seed and twelve are select seed from known half-sib orchard families. The enormous differences in behavior constituting two full orders of magnitude, especially within the non-select seed, are immediately apparent. As has been noted earlier, similar results have been obtained with *Pinus taeda*, although not all genotypes have been processed to the later stages of treatment at the present time.

While the plant growth hormone usages noted in Table 2 are near optimum for loblolly pine, different concentrations and mixtures may prove more suitable for other species. It is fairly well established that growth hormones are usually necessary in Stages I-III, although some workers have apparently achieved early stage proembryos using growth hormone-free media. However, even when initially cultured on hormone-free media, these early stage proembryos were then transferred to cultures having the usual growth hormones. These hormones may in some instances be a single auxin or a mixture of auxins with or without one or more cytokinins. As a general rule the total concentration of all growth hormones should be below about 250 $\mu$M/L, preferably below about 100 $\mu$M/L in the Stage I medium. These concentrations should be reduced about tenfold in the Stage II and Stage III media.

The following tables show preferred media for culture of Norway spruce by somatic embryogenesis.

TABLE 4

Picea Abies Basic Culture Media

| Constituent | Concentration, mg/L A[1] | Concentration, mg/L B[2] |
|---|---|---|
| BASAL SALTS | | |
| $NH_4NO_3$ | — | 206.3 |
| KCl | 372.5 | — |
| $KNO_3$ | 50.0 | 2340.0 |
| $KH_2PO_4$ | 85.0 | 85.0 |
| $MgSO_4.7H_2O$ | 160.0 | 185.0 |
| $CaCl_2.6H_2O$ | 220.0 | 220.0 |
| KI | 0.415 | 0.415 |
| $H_3BO_3$ | 3.10 | 3.10 |
| $MnSO_4.H_2O$ | 8.45 | 8.45 |
| $ZnSO_4.7H_2O$ | 4.30 | 4.30 |
| $NaMoO_4.2H_2O$ | 0.125 | 0.125 |
| $CuSO_4.5H_2O$ | 0.0125 | 0.0125 |
| $CoCl_2.6H_2O$ | 0.0125 | 0.0125 |
| $FeSO_4.7H_2O$ | 13.90 | 13.93 |
| $Na_2EDTA$ | 18.65 | 18.63 |
| ORGANIC ADDITIVES | | |
| Sucrose | 10,000. | 30,000. |
| myo-Inositol | 50.0 | 1000.0 |
| Casamino acids | 500.0 | 500.0 |
| L-Glutamine | 750.0 | 450.0 |
| Thiamine.HCl | 0.05 | 1.00 |
| Pyridoxine.HCl | 0.05 | 0.50 |
| Nicotinic acid | 0.25 | 0.50 |
| Glycine | — | 2.00 |
| L-Asparagine | 50.0 | — |
| pH | 5.8 | 5.7 |

[1]Institute of Paper Chemistry medium (Becwar, Noland, and Wann 1987)
[2]Gupta and Durzan medium $BM_3$ (1986b).

TABLE 5

Composition of Picea Abies Media for Different Stage Treatments $BM_I$—Induction Medium
  $BM_A$[1] + NAA[3] (10.8 μM) + BAP[4] (4.4 μM) + 7.0 g/L Difco agar.

$BM_M$—Maintenance and Multiplication Medium
  $BM_B$[2] + 2,4-D[5] (5 μM) + BAP (2 μM) + KIN[6] (2 μM). 6.0 g/L Difco agar added if solid medium is desired.

$BM_D$—Cotyledonary Embryo Development Medium
  $BM_B$ + 40.0 mg/L Arginine + 100 mg/L Asparagine + 6.0 g/L Tissue Culture Agar + Abscisic acid (as specified) + Adsorbent (e.g., activated charcoal) (as specified). $KNO_3$ is reduced to 1170 mg/L in basal salts.

$BM_G$—Germination Medium
  $BM_B$ with $KNO_3$ reduced to 1170 mg/L, myo-Inositol reduced to 100 mg/L, Sucrose reduced to 20.0 g/L, and L-Glutamine and Casamino acids removed. 2.5 g/L of Adsorbent and 6.0 g/L of Tissue Culture Agar are added.

[1]Basic medium A from Table 4
[2]Basic medium B from Table 4
[3]2-Naphthylacetic acid (Naphthalene-2-acetic acid)
[4]$N^6$-Benzylaminopurine
[5]2,4-Dichlorophenoxyacetic acid
[6]Kinetin

EXAMPLE 4

The following screening experiment was made as a comparison between embryo development stage cultures containing only abscisic acid as a hormone additive with cultures containing a mixture of abscisic acid and activated charcoal. Mature Picea abies seed embryo explants were cultured on an Initiation Medium and Maintenance Medium as described in Tables 4 and 5. Explants were incubated in light of an intensity approximately 50 $\mu Em^{-2}sec^{-1}$. In this case the Induction Medium $BM_I$ had a relatively low carbohydrate content with a resulting low osmolarity of about 62 mM/kg. After an early stage embryogenic mass had developed, it was transferred to a solid and later to a liquid liquid Maintenance and Multiplication Medium $BM_M$ having a higher osmolarity of about 158 mM/kg. In this case the proembryos had attained a sufficiently late stage of development without the need for further culturing on a very high osmotic potential Late Proembryo Development Medium. These proembryos were settled and washed twice with liquid Embryo Development Medium $BM_D$ of Table 5 to which 10 mg/L of abscisic acid had been added. The washed cells were then drained on polyester pads. Approximately 2 mL of the washed cells were transferred to solid Embryo Development Medium $BM_D$ on 50 mm petri dishes. The growing cells were transferred twice at two week intervals to fresh media of the same composition. Culture room conditions were about 23°-24° C. in darkness throughout the experiment. The following table shows the compositions of the media used and the results obtained.

TABLE 6

| Medium Composition $BM_D$ | | Cotyledonary Embryos, |
|---|---|---|
| ABA, mg/L | Activated charcoal, g/L | Average Yield/2 mL |
| 2.0 | 0 | 18.6 |
| 5.0 | 0 | 20.0 |
| 7.5 | 0 | 13.0 |
| 10.0 | 0 | 12.9 |
| 25.0 | 0 | 14.7 |
| 25.0 | 2.5 | 2.0 |
| 150.0 | 2.5 | 4.1 |
| 100.0 | 2.5 | 16.1 |
| 250.0 | 2.5 | 0.1 |

The ABA/charcoal media did not in general produce as many cotyledonary embryos in this experiment as the media with ABA alone. However, it was noted that the embryos produced on the media containing charcoal were frequently larger and of superior morphology to those cultured on the media containing only ABA. This experiment showed that embryos could be successfully cultured on media having relatively high concentrations of ABA and activated charcoal. Further, there was an indication that these embryos would have superior strength to those cultured on media containing only ABA.

It was noted during the experiment that development and mass growth on the charcoal containing media was so rapid that 10–14 days after starting the experiment most growth had stopped and the mass containing the embryos appeared dry. This suggested that available liquid was absorbed during early growth and may have become limiting.

The above experiment was carried out on three additional genotypes of Picea abies. In these tests no preliminary washes with ABA-containing medium were given. Results were variable. One genotype produced no cotyledonary embryos under any conditions. Another produced an average of 10.2 embryos on the media without charcoal and only 0.4 embryos on the charcoal containing media. The third genotype produced an average of only 1.7 embryos on the ABA only media and 2.0 embryos on the charcoal containing media.

It should be noted that the above reported experiments were of a preliminary screening nature only and do not represent optimized conditions. They were primarily made to see if the use of activated charcoal in the cotyledonary embryo development stage would be advantageous.

EXAMPLE 5

In a followup experiment to that just described, five genotypes of Picea abies were cultured as described above using a solid cotyledonary development medium containing 100 mg/L ABA and 2.5 g/L activated charcoal. This time the liquid $BM_M$ medium containing the proembryos was simply settled and the supernatant liquid poured off. Then 2 mL of the settled cells were pipetted onto the surface of the solid medium without washing or further draining in order to provide additional water for the system.

Embryos were visible within two weeks and harvestable by 3½ weeks. One genotype produced 34 robust cotyledonary embryos per mL of settled cells. Another produced 5.3 embryos per mL. The other genotypes produced few or no embryos.

160 cotyledonary embryos of the best performing genotype were transferred to a germination medium, incubated three weeks in the dark, transferred to fresh media and moved to the light. About 25% of these embryos began epicotyl development after five weeks.

Again, it should be noted that no optimization of the ABA-charcoal ratio had been attempted.

EXAMPLE 6

Another set of experiments was made under conditions similar to the previous example in which activated charcoal in the cotyledonary embryo development medium was varied between 0 and 2.5 g/L and ABA varied between 5 and 100 mg/L. Four genotypes of Picea abies was used in the experiment. At least five replicates were made at each test condition.

Media compositions are given in the following table.

TABLE 7

| Medium No. | ABA, mg/L | Charcoal g/L | Average Embryos/mL, Genotype | | | |
|---|---|---|---|---|---|---|
| | | | A | B | C | D |
| 1 | 100 | 2.5 | 46 | 0 | 0.5 | 13.2 |
| 2 | 50 | 1.25 | 102 | 0 | 1.8 | 9.5 |
| 3 | 10 | 0.25 | 76 | 0 | 0.6 | 20.4 |
| 4 | 10 | 0.10 | 18 | 0 | 0.2 | 5.4 |
| 5 | 5 | 0.0 | 0 | 0 | 0 | 0 |

Medium No. 2 containing 50 mg/L ABA and 1.25 g/L activated charcoal appeared to be significantly better than the others from the standpoints of number and vigor of embryos formed.

In a further modification of this experiment the best performing genotype above (Genotype A) was transferred onto the medium supported on laboratory filter paper. The experiment was replicated using the same culture media as above. As is seen in the following table, the results of cultures grown on agar medium alone and on filter paper supported on agar media are generally comparable. This opens up the possibility of direct mass transfer to germination or other media with a considerable savings in handling required. It further opens the possibility of a system in which either the charcoal or ABA is located on the filter paper with the other component being in the medium.

TABLE 8

| Medium No. | ABA, mg/L | Charcoal, g/L | Average Embryos/mL, | |
|---|---|---|---|---|
| | | | Directly on Agar | On Filter Paper |
| 1 | 100 | 2.5 | 46 | 43 |
| 2 | 50 | 1.25 | 102 | 93 |
| 3 | 10 | 0.25 | 75 | 55 |
| 4 | 10 | 0.10 | 17 | 30 |
| 5 | 5 | 0.0 | 0 | 0 |

EXAMPLE 7

A comparison was made using four methods of culturing Picea abies at the embryo development stage. The first method used Embryo Development Media containing both ABA and activated charcoal. One subset was a replication of the Medium 2 composition from the previous example that gave the best results. Another subset used reduced amounts of both ABA and activated charcoal. In the second method the charcoal was omitted from the culture medium but the late stage proembryos were first coated with activated charcoal by rinsing them with a charcoal-containing liquid medium. The third method first cultured the late stage proembryos on a medium containing only activated charcoal followed by culturing on a medium containing only ABA. Finally, cultures were made on ABA-containing medium without any charcoal. In one subset of this method the growing embryos were transferred three times to fresh medium. In the other subset the embryos remained on the original medium the entire culturing period.

Two new genotypes of Picea abies not tested in the earlier examples were used for the present set of experiments. Results are given below. The compositions of all the media used are given in the Table 9. Late stage proembryos, cultured as in the last three examples, were used for all trials.

TABLE 9

| Medium No. | Composition |
|---|---|
| 1 | $BM_D$ (Table) + 15 mg/L ABA + 0.75 g/L activated charcoal |
| 2 | $BM_D$ + 50 mg/L ABA + 1.25 g/L activated charcoal |
| 3 | $BM_M$ without hormones or agar + 2.5 g/L activated charcoal |
| 4 | $BM_D$ + 10 mg/L ABA |
| 5 | $BM_D$ + 15 mg/L ABA |
| 6 | $BM_D$ + 10 g/L activated charcoal |
| 7 | $BM_D$ + 5 mg/L ABA |

PROCEDURES AND RESULTS

First Method—ABA/Activated Charcoal Medium 1.0 mL of settled late stage proembryos was pipetted directly onto replicate 5 cm plates of media 1 and 2 above and cultured in the dark at about 22° for six weeks.

| Embryos Produced | Genotype A | Genotype B |
|---|---|---|
| Medium 1 | 54.0 | 26.3 |
| Medium 2 | 83.0 | 92.5 |

These embryos had improved apical domes, hypocotyl region and root primordia when compared with embryos cultured on a development medium using ABA alone. Also a greater number of embryos were produced using the charcoal containing media. Ultimately the germination rate and successful growth into plantlets was also increased over a control group grown without activated charcoal.

Second Method—Activated Charcoal Coated Embryos on ABA Medium

Settled late stage proembryos were suspended in Medium 3 above, settled, and then 1.0 mL was pipetted onto replicate 5 cm plates of media 4 and 5 above. Most of the activated charcoal in the rinse medium was retained with the settled proembryos. These were also cultured in the dark for six weeks at about 22° C.

| Embryos Produced | Genotype A | Genotype B |
| --- | --- | --- |
| Medium 4 | 0.0 | 1.0 |
| Medium 5 | 11.8 | 35.8 |

These embryos also had the improved morphology noted for those produced by the first method.

Third Method—Activated Charcoal Medium then ABA Medium 1.0 mL of settled late stage proembryos was pipetted directly onto replicate 5 cm plates of medium 6 (activated charcoal only). These were cultured for one week at 22° C. in the dark then were transferred to medium 7 (ABA only) for five weeks. No cotyledonary embryos were produced for either genotype.

Fourth Method—ABA Medium With and Without Transfers 1.0 mL of settled late stage proembryos was pipetted directly onto replicate 5 cm plates of medium 7 (ABA only). These were cultured in the dark at about 22° C. One subset was maintained on the original medium for the entire six week period. The other subset was transferred to fresh medium of the same composition at the end of the second and fourth weeks, then maintained on the last medium until the end of the test.

| Embryos Produced | Genotype A | Genotype B |
| --- | --- | --- |
| Not transferred | 0.0 | 0.0 |
| Transferred | 2.0 | 3.3 |

The few cotyledonary embryos that developed were of poorer quality than those developed using the first and second methods. They did not show the prominent apical domes and had a shorter, often bulging, shape.

It is very evident that the combination of ABA and activated charcoal in the Embryo Development Medium is highly advantageous from the standpoint of both numbers and quality of embryos produced. It appears that the charcoal is most effective when it is uniformly dispersed throughout the medium. However, it is also advantageous when it is localized around the growing embryos. It is believed that the charcoal could also be localized on the upper surface of the medium with similar good results. For example the activated charcoal could be on a filter paper or other type porous membrane which might also be used as a support surface for the growing embryos. It should be noted here that none of the media compositions used are represented as being optimized for any of the genotypes employed.

To the present time, using the procedures just outlined, about 3800 plantlets of *Picea abies* have been produced from 20 different genotypes of the species and established in soil.

The use of the combined ABA-activated charcoal systems gave an additional entirely unexpected advantage. Somatic embryos generated on these media could be stored for extended periods of time at 4°–5° C. while remaining on the Embryo Development Medium. A number of genotypes of both *Pinus taeda* and *Picea abies* have now been stored for over three months without any evident deterioration or loss of vigor. Embryos of *Pseudotsuga menziesii* have been stored only for shorter periods at the present time but they too seem to have retained full vigor. These stored embryos develop normally into plantlets when moved to a rooting medium. Storage temperatures from just above the freezing point of the embryos (approximately 0° C.) to about 10° C. appear to be very satisfactory. It would appear that the temperature needs to be lowered only sufficiently to essentially inhibit metabolic action within the embryos. Storage is preferably done in the dark or on low light conditions. Prior to the present time long term storage usually required desiccation (e.g., see Buchheim, Colburn and Ranch 1989) or alginate gel encapsulation (e.g., Gupta and Durzan 1987).

DOUGLAS FIR CULTURE

A number of observations in the laboratory led to the hypothesis that considerably raised osmotic levels would be advantageous in the embryo development stage of Douglas-fir, and perhaps other difficult to culture species as well. Very high osmotic levels would tend to gradually remove moisture from the developing embryos. This might provide an analogous situation to the later stages of embryo development experienced in the formation of a natural seed. Prior to this time Douglas-fir cultures used a development medium containing 2-3% sucrose and having an osmotic potential in the 130-160 mM/kg range. The resulting somatic embryos were generally of poor quality and the conversion rate to rooted plants was low. The experiments outlined in the following examples were designed to test the above hypothesis and to optimize conditions if results were encouraging.

Figure 6:
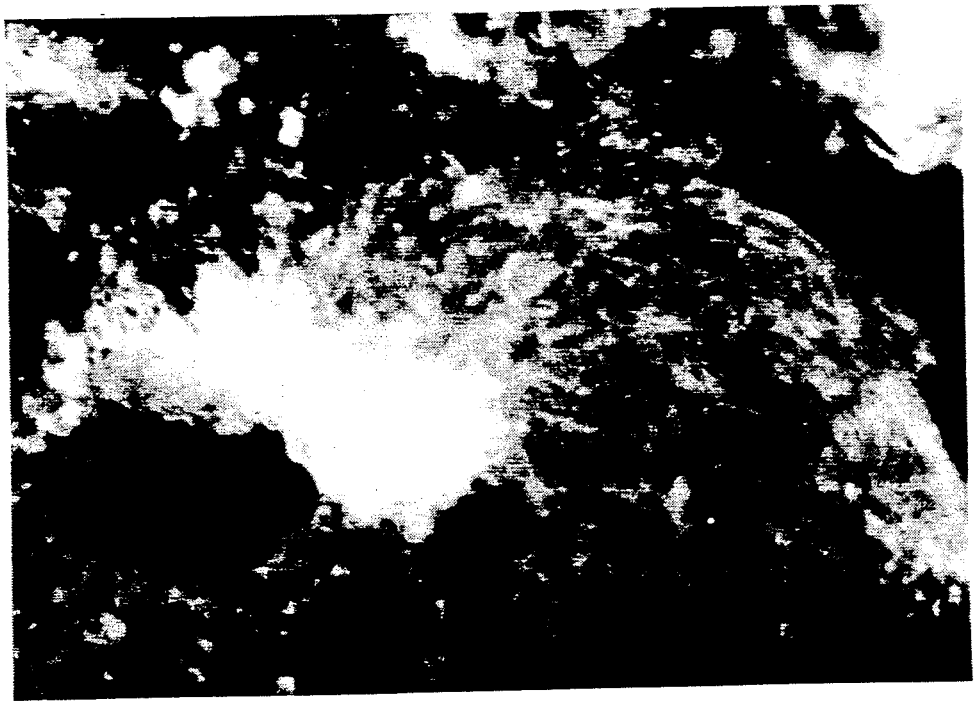
FIG. 6 is a photomicrograph of a clump of Douglas-fir early proembryos.
Figure 7:
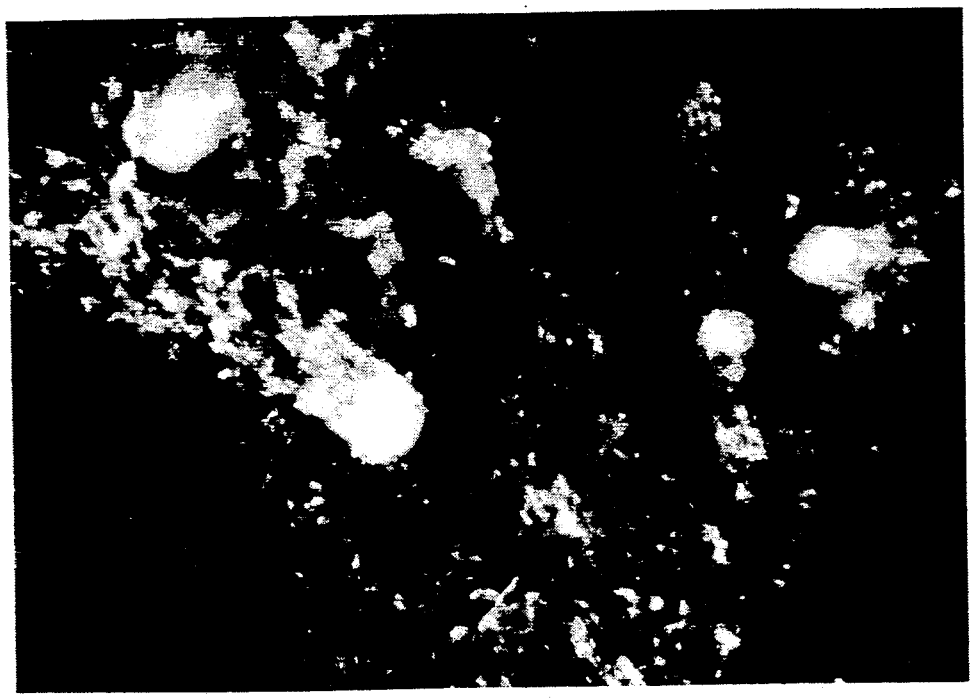
FIG. 7 is a photomicrograph of embryos after singulation.
Figure 8:
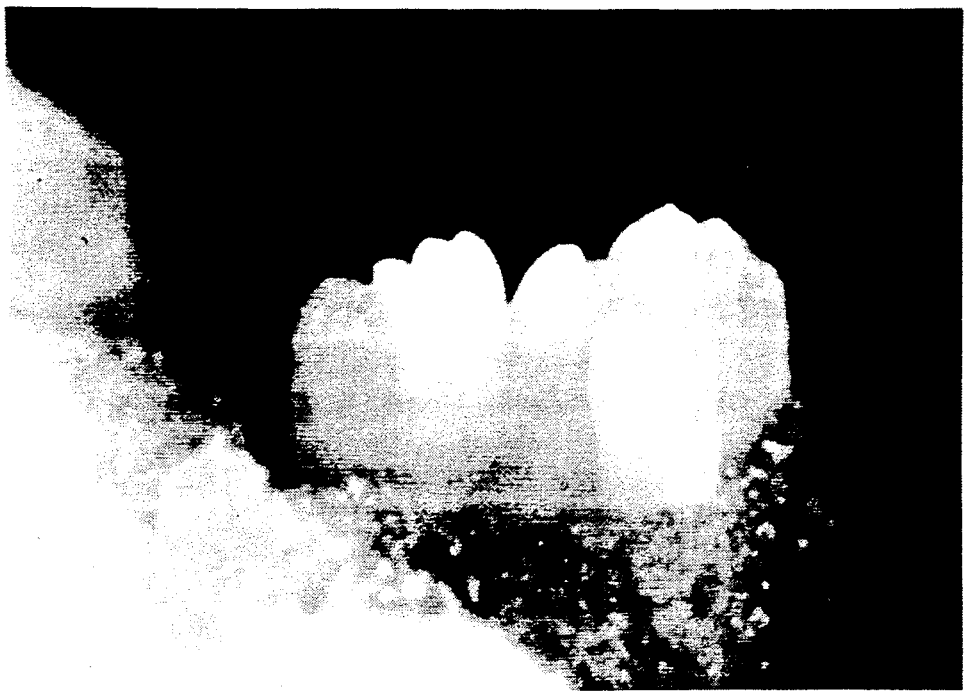
FIG. 8 is a photomicrograph of a clump of unsingulated Douglas-fir cotyledonary embryos.

As noted in the background discussion, the embryogeny of Douglas-fir is quite different from trees such as the spruces or pines. One of these differences is seen when early stage proembryos are placed in or on a late stage proembryo development medium. Instead of single late stage embryos, Douglas-fir develops tight clumps of these embryos, as is shown in the photomicrograph of FIG. 6. Upon further development into cotyledonary embryos, these clumps remain united and the resulting product is useless for further conversion (FIG. 7). This phenomenon had apparently been recognized earlier by Durzan and Gupta (1987) who, while they did not discuss it specifically, transferred their embryonal-suspensor masses to a liquid shake culture containing 0.5 $\mu$M abscisic acid. They note that under the influence of ABA, individual bipolar embryos were produced which were then transferred to a development medium without ABA. The present method utilizes a liquid shake culture with reduced osmotic level and added abscisic acid between late proembryo development and cotyledonary embryo development to achieve the necessary singulation.

A reformulated basal culture medium has been developed by the present inventors specifically to give more successful initiation and multiplication of Douglas-fir. Preferred media compositions are given in the following tables. A number of ingredients, such as those that affect the level and balance between organic and inorganic nitrogen, are varied in quantity depending on the response of individual genotypes. This response cannot be readily predicted and media optimization must largely be achieved by a combination of intuition and trial and error.

TABLE 10

Pseudotsuga Menziesii Basic Culture Media

| Constituent | Concentration, mg/L | |
|---|---|---|
| | WTC[1] | BM$_G$[2] |
| BASAL SALTS | | |
| NH$_4$NO$_3$ | — | 206.3 |
| KNO$_3$ | varies[1] | 1170.0 |
| CaCl$_2$.6H$_2$O | 200.0 | 220.0 |
| Ca(NO$_3$)$_2$.2H$_2$O | varies[1] | — |
| KH$_2$PO$_4$ | 340.0 | 85.0 |
| MgSO$_4$.7H$_2$O | 400.0 | 185.0 |
| MnSO$_4$.H$_2$O | 20.8 | 8.45 |
| ZnSO$_4$.7H$_2$O | 8.0 | 4.30 |
| CuSO$_4$.5H$_2$O | 0.024 | 0.013 |
| FeSO$_4$.7H$_2$O | 27.85 | 13.93 |
| Na$_2$EDTA | 37.25 | 18.63 |
| H$_3$BO$_3$ | 5.0 | 3.10 |
| NaMoO$_4$.2H$_2$O | 0.20 | 0.125 |
| CoCl$_2$.6H$_2$O | 0.025 | 0.0125 |
| KI | 1.00 | 0.42 |
| AlCl$_3$ | 0.02 | — |
| ORGANIC ADDITIVES | | |
| myo-Inositol | varies[1] | 100.0 |
| Thiamine.HCl | 1.00 | 1.00 |
| Nicotinic acid | 0.50 | 0.50 |
| Pyridoxine.HCl | 0.50 | 0.50 |
| Glycine | 2.00 | 2.00 |
| L-Glutamine | varies | 450.0 |
| Casamino acids | 500.0 | — |
| Sucrose | varies | 20,000. |
| pH | 5.7 | 5.7 |

[1] Usage varies according to culturing stage and genotype.
[2] Modified Gupta and Durzan medium BM$_3$ (1986b). Medium BM$_G$ of application Serial No. 426,331.

TABLE 11

| | Stage I Initiation | Stage II Maintanance 1 | Stage III Maintanance 2 | Stage IV Singulation | Stage V Development | Stage VI Germination |
|---|---|---|---|---|---|---|
| KNO$_3$ | 1250[1] | 1250-2500 | 1250 | 1050 | 2000-2500 | 1170 |
| Ca(NO$_3$)$_2$.2H$_2$O | — | — | — | 200 | — | 220 |
| myo-inositol | 1000 | 1000 | 1000-30,000 | 100 | 100 | 100 |
| L-Glutamine | 450 | 450 | 1000 | 1000 | 750-1500 | — |
| Amino acid mixture[2] | — | — | — | — | 290 | — |
| Sucrose | 15,000 | 30,000 | 30,000 | 20,000 | 20,000 | 20,000 |
| Supp. carbohydrate | — | — | — | — | 30,000-300,000 | — |
| 2,4-D | 110 | 1.1 | 1.1 | — | — | — |
| N6-Benzyladenine | 45 | 0.22 | 0.22 | — | — | — |
| Kinetin | 43 | 0.22 | 0.22 | — | — | — |
| Abscisic acid | — | — | — | 0-15 | 5-50 | — |
| Activated charcoal | 2500 | — | — | — | 250-2500 | 2500 |
| Agar | 5000 | 5000 | — | — | — | 8000[4] |
| Gelrite | — | — | — | — | 3000[3] | — |

[1] All units are in mg/L (or ppm).
[2] L-Proline - 100, L-Asparagine - 100, L-Arginine - 50, L-Alanine - 20, L-Serine - 20.
[3] Not used for liquid media.
[4] Tissue culture agar.
The pH of all media are adjusted to 5.7.

It will be seen by reference to the media compositions that the features of the earlier inventions described in our parent applications have been advantageously retained. A raised osmotic pulse is still advantageous for good quality late proembryo development. This level will differ somewhat between species and even between genotypes within each species. Similarly, the cotyledonary embryo development medium should contain the same combination of abscisic acid and activated charcoal found so desirable with Norway spruce and loblolly pine.

The examples that follow represent steps in the evolutionary process of formulating a Douglas-fir development medium that represents the best mode known at present for culturing this species by somatic embryogenesis. These examples are all directed to the cotyledonary development stage. The steps prior to that time are similar to those used for loblolly pine and Norway spruce with the exceptions of the now essential embryo singulation stage and somewhat reformulated media. These earlier steps will be briefly outlined.

A preferred explant for Douglas-fir is an immature zygotic embryo. Best results have been realized with embryos selected just prior to the development of an apical dome up to the time just before cotyledon primordia become visible. The cones are split longitudinally and seeds isolated from young ovuliferous scales. Seeds are sterilized by first being agitated in 10% Liqui-Nox laboratory cleaner (Alconox, Inc, New York, N.Y. with a small additional amount of liquid surfactant for about 10 minutes. They are then rinsed in running tap water for 30 minutes. At this time they are transferred to a sterile hood and agitated in 20% H$_2$O$_2$ for 10 minutes. Following five rinses in sterile deionized water the seed coat is split and the female gametophyte removed. This is split on one side and the embryo teased out while still remaining attached to the gametophyte by the suspensor. An explant so prepared is placed on the Stage I' solid initiation medium in a 50 mm petri dish. The explants are incubated in the dark from 4-8 weeks. Success in forming an embryonal-suspensor mass (ESM) containing proembryos varies from about 1-7% depending on a number of variable factors which presently are not well understood.

All stages of culture are carried out at temperatures which may vary between about 20°-25° C. Temperature is not generally critical and may, on occasion be varied so as to fall outside this range.

The embryonal-suspensor masses containing early stage proembryos are transferred to a solid Stage II maintenance and multiplication medium containing greatly reduced plant growth hormones and preferably a somewhat raised osmotic level. Again, culturing is carried out in the dark with subcultures made at no greater than about two week intervals. The clone can be maintained at this stage for long periods of time.

Early stage proembryos from the multiplication step are transferred to a liquid Stage III second maintenance medium Having a significantly raised osmotic level. This corresponds to the raised osmotic pulse found so beneficial for loblolly pine. It is similarly advantageous for Douglas-fir and Norway spruce. However, a slightly lower osmotic level of at least about 170 mM/kg will usually suffice for Douglas-fir although some genotypes may require levels as high as 240 mM/kg. Myo-inositol, which will normally be around 5000 mg/L, may need to be adjusted somewhat depending on the needs of the particular genotype in order to obtain optimum results. Culture is carried out in the dark and is periodically subcultured, usually weekly. Robust late stage proembryos having 100 or more cells will develop during this time.

Following late proembryo development, the cultures are transferred to a Stage IV liquid medium for the singulation step referred to earlier. This has a reduced osmotic level and is free of auxins and cytokinins. Abscisic acid is a newly added hormone in an initial amount in the range of about 5-15 ppm, more usually the lower level. Cultures are again carried out in the dark. From two to four subcultures are made on a weekly basis. The level of exogenous abscisic acid will drop somewhat during each subculture. It is important that the level of abscisic acid at the beginning of a new subculture not be significantly higher than the level at the end of the previous subculture. This will result in an essentially continuous drop in ABA level over the singulation period. At this time the embryos are ready to begin development to cotyledonary embryos. They are transferred to either a solid or liquid medium with an effective abscisic acid level which again is not significantly higher than that at the end of the final singulation subculture. Most typically this will be about 5-6 ppm effective ABA for cultures on solid medium but it may be lower. In some cases it is not necessary to add exogenous ABA to the development medium since a sufficient amount will be carried over with the residual medium accompanying the embryos when the transfer is made from the last singulation stage. However, it is always necessary for some activated charcoal to be present in the development medium. It has been found preferable for Douglas-fir to carry out development cultures entirely in the dark.

EXAMPLE 8

A basal Douglas-fir development medium was modified by addition of 1, 2, or 3% myo-inositol, 2% sucrose, 2% sorbitol, or 2% mannitol to determine the effect of these osmoticants on embryo development. The above noted sucrose and myo-inositol was in addition to that normally present in the development medium. All media contained 0.5% activated charcoal and 5 ppm abscisic acid and were gelled with 5 g/L tissue culture agar. Each culture plate received 1 mL of settled singulated cells. Five genotypes were cultured using triplicate plates for most genotypes. While successful development was not obtained on all genotypes, a clearly superior response was achieved on the media containing 2% sorbitol.

It is known that activated charcoal is an effective adsorbent of plant hormones in culture media. For example, we showed earlier that charcoal can effectively reduce over time the level of exogenous abscisic acid available to developing embryos. Until the present, the rate and magnitude of this effect has not been well known.

ABA concentration in liquid media can be studied using known analytical methods that determine ABA concentration by measurement of ultraviolet absorption. Nitrate is an interfering ion so the liquid media for the following tests were made up without any inorganic nitrogen present. Present studies have shown that when ABA is added to a charcoal-containing liquid medium there is an immediate drop in the level of available ABA. As would be expected, with a constant amount of activated charcoal present, the effect is more pronounced when only small quantities of ABA are added. In the following tests, stirred Norway spruce liquid development media with nitrates omitted were sampled at various times after addition of ABA. All media contained 0.075% activated charcoal. The ABA added increased in 5 ppm steps from 5 to 25 ppm total addition.

TABLE 12

| ABA Added, ppm | Percentage of Originally Added Abscisic Acid Remaining Available | | | |
|---|---|---|---|---|
| | Time after ABA Addition, minutes | | | |
| | 0 | 1 | 5 | 10 |
| 5 | 39 | 35 | 16 | 9 |
| 10 | 50 | 34 | 17 | 13 |
| 15 | 60 | 41 | 24 | 19 |
| 20 | 57 | 44 | 25 | 20 |
| 25 | 68 | 46 | 29 | 24 |

It is evident from the above data that when ABA levels are discussed in a charcoal-containing system only available or free ABA levels should be considered.

Not surprisingly, it was also found that activated charcoal of different grades and sources adsorbed ABA at different rates. In a companion experiment to the above, charcoal from four suppliers was tested. An ABA solution of known concentration was added to a liquid medium with stirring and measurements of free ABA were made over a 24 hour period. In all cases 50 ppm ABA was added. Charcoal concentration was 0.125%. About 250 mL of medium was made up in a 400 mL beaker. The medium was stirred for 10 minutes and then the charcoal was allowed to settle and the supernatant liquid was sampled at the indicated times. As was also the case with the first example, all suspended charcoal was immediately filtered from the liquid samples before further analysis. Results were as follows.

TABLE 13

| Charcoal Source | Amount of Originally Added Abscisic Acid Remaining Available, ppm | | | | |
|---|---|---|---|---|---|
| | Time after ABA Addition | | | | |
| | 0 min | 5 min | 10 min | 30 min | 24 hours |
| A | 27 | 11 | 9 | 9 | 6 |
| B | 31 | 20 | 17.5 | 17.5 | 12.5 |
| C | 41 | 30.5 | 30 | 29.5 | 25 |
| D | 44 | 44 | 43 | 43 | 34 |

It is evident that different sources and/or grades of charcoal behave in very different manners in regard to adsorption rates of abscisic acid. Thus the type or brand of activated charcoal should be precisely specified if consistent results are to be expected. Charcoal A was used in the preceeding example and throughout all of the work described herein. It is available from Sigma Chemical Co., St. Louis, Mo. as their Catalog No. C-4386 and is described as HCl washed. This is not intended to be an endorsement of this product over others that would undoubtedly be equally suitable but merely sets the specific identify of the product used in the examples.

Measurement of ABA in solid media presented a much more difficult problem than measurement in a liquid system. Normally it would involve a tedious and complex extraction process. However, the extraction method would not be suitable in an environment where the ABA concentration was changing rapidly. The following method has been developed and has proved very suitable. A small amount of tritium labeled abscisic acid is added to the normal abscisic acid used for making up the media. $^3$H labeled ABA is available from Amersham Corp., Arlington Heights, Ill. After pouring the plates and allowing the media to solidify and cool, a quadrant (¼ circle) of a 42.4 mm diameter filter paper is placed on the surface of the gelled medium for approximately 10 seconds. In this period of time the filter paper will imbibe about 0.43–0.47 g of liquid from the medium. The moist paper is removed with tweezers and placed in a vial suitable for counting in a scintillation counter. All samples are normalized to a pickup of 0.45 g of liquid medium. The amount of radioactivity on the filter paper can be can be related to the total amount of available or free abscisic acid in the medium.

It was assumed that rates of ABA adsorption by activated charcoal would be different in solid and liquid media. The following experiment was designed to show free ABA in a development medium solidified by 3% Gelrite Gellan Gum. Gelrite gum is a microbially produced heteropolysaccharide and is available form Chemical Dynamics Corp., South Plainfield, N.J. One medium was made using 0.125% activated charcoal. An equivalent medium was made without charcoal for comparison. The media were formulated with the gellant and sterilized by autoclaving. After cooling to about 55°–60° C., a filter sterilized solution equivalent to 40 ppm of ABA in the medium was added. The ABA solution included an appropriate aliquot of the tritiated ABA. The mixture was then stirred for either 1 minute or 10 minutes before being pipetted into 50 mm petri dishes and allowed to cool. Abscisic acid content of the gelled medium was measured 2 hours and 24 hours after pouring and again after 5 days. Results were as follows.

TABLE 14

Abscisic Acid Availability Over Time in Solid Culture Media

| Time of Measurement | Stirring Time, min | Effective ABA Concentration, ppm | |
|---|---|---|---|
| | | With Charcoal | Without Charcoal |
| 2 hrs | 10 | 9.0 | ~40 |
| 2 hrs | 1 | 14.5 | ~40 |
| 24 hrs | 10 | 5.7 | ~40 |
| 24 hrs | 1 | 6.6 | ~40 |
| 5 days | 10 | 4.2 | ~40 |

The short term drop in abscisic acid in the charcoal containing samples is again quite dramatic. No loss of ABA was seen in the medium without activated charcoal. It is clearly evident that in any charcoal containing medium it is the *effective* or *free* amount of abscisic acid, and undoubtedly other hormones as well, that must be considered. The amount of added hormone is meaningful only when all other parameters are defined.

Osmotic potential of the various media is measured using a Wescor 5500 Vapor Pressure Osmometer. This is available from Wescor, Inc., Logan, Utah. Osmotic potential of liquid media is measured by placing a 6.5 mm circle of filter paper on the sample tray of the instrument and adding a measured 10 μL of medium. For solid media, the filter paper circles are placed on the surface of the gelled media where they imbibe a sufficient amount of liquid for measurement.

EXAMPLE 9

Further experiments carried out on the basis of the results described in the previous example confirmed the beneficial effects of 2% sorbitol used in the development media. However, sorbitol concentrations in the 3–4% range, while giving lower embryo yields in terms of numbers, did appear to improve quality. The embryos were more similar in appearance to zygotic embryos.

It had been observed elsewhere that the use of a gelling material other than agar in the development cultures improved embryo yield and quality. In the following tests tissue culture agar had been replaced with Gelrite Gellan Gum. Its use as a medium gellant in tissue culture is not new, although it is not believed to have been used before in a medium similar to the present embryo development medium. As one hypothesis for its superior performance, its faster gelling rate, compared with agar, is believed to reduce the initial adsorption rate of abscisic acid by the activated charcoal present in the medium.

Experiments were then carried out in which from 2–6% sorbitol was used in a basal Douglas-fir development medium in combination with 0.3% Gelrite gum. Other variable components were 2500 ppm KNO$_3$, 750 ppm L-glutamine, 5 ppm abscisic acid, and 0.05% activated charcoal. The media were mixed one minute after the addition of abscisic acid and poured into petri dishes. Embryos were plated approximately 24 hours later. Five genotypes were used with four replicates per genotype per treatment. Summary results are given in the following table.

TABLE 15

| Sorbitol, % | Osmotic Potential, mM/kg | Average Number of Somatic Embryos Formed Genotypes | | | | |
|---|---|---|---|---|---|---|
| | | 738 | 742 | 735 | 676 | 733 |
| 2 | 277 | 0.8 | 6.0 | 14.5 | 0.0 | 0.3 |
| 3 | 341 | 12.0 | 4.0 | 18.3 | 2.5 | 0.0 |
| 4 | 402 | 30.3 | 19.5 | 19.5 | 4.0 | 0.0 |
| 4.5 | 426 | 26.8 | 9.0 | 9.0 | 2.0 | 0.3 |
| 5 | 471 | 37.7 | 26.3 | 22.0 | 2.8 | 0.0 |
| 6 | 528 | 7.8 | 15.5 | 22.5 | 0.0 | 0.0 |

Depending on genotype, it appears that in combination with Gelrite gum, sorbitol is beneficial as an osmoticant at concentrations at least as high as 6%. Both yield and quality were improved. Embryos were compact and yellow and more similar to zygotic embryos than those developed previously. Osmotic levels above 400 mM/kg were the highest investigated to that time. The performance in this higher range tends to support the earlier stated hypothesis.

EXAMPLE 10

Sorbitol is known to be poorly metabolized by embryos in culture. Its effect noted above is believed to be primarily osmotic. However, it also apparently presents a favorable chemical environment as well since the other osmoticant materials screened earlier (Example 8) showed definitely inferior performance. Subsequent to the work just reported, polyethylene glycol (PEG), with an average molecular weight of about 8000, was evaluated and found to be a superior osmoticant. It is assumed that there is no metabolism of the PEG by the developing plant and the reasons for its superior performance, compared with other materials, is not entirely clear. Very high levels of PEG, up to about 30%, have been found useful in liquid media. When more than about 12% PEG is used in a solid medium there is a tendency to inhibit gelation. Polyethylene or polypropylene glycols of other molecular weights are believed to be equally useful. Upper and lower limits of molecular weight which are useful have not yet been determined.

In order to determine the optimum level of PEG a Stage V liquid development medium having 2500 ppm KNO$_3$, 1000 ppm L-glutamine, and 0.1% activated charcoal but no abscisic acid was made up with polyethylene glycol 8000 percentages varying between 15 and 30% (150,000–300,000 mg/L). A 40×40 mm polyester pad was dipped into each medium so as to pick up about 5–5.5 mL of the medium which was kept continuously mixed to keep the charcoal in uniform suspension. The pads were cut from polyester batting having a thickness of about 4 mm and a basis weight of about 150 g/m$^2$. Each saturated pad was placed in a 120 mm petri dish.

Singulated Douglas-fir late stage proembryos were settled and excess medium removed. The cells were rinsed with an equal volume of the development medium of similar composition to that on which they were to be placed. The rinse liquid did not contain any charcoal or PEG but did contain 2.5 ppm ABA.. The cells were again settled and half of the supernatant liquid removed (¼ of the total volume). The cells were again resuspended in the remaining liquid and 1.5 mL was placed on the medium saturated polyester pad. The effect of the contained liquid transferred with the cells was to dilute the osmoticant contained within the pad. This dilution is taken into account in determining the effective osmotic level after dilution. The only exogenous ABA supplied was that which was transferred with the cells from the rinse liquid. Table 16 which follows gives experimental conditions and results.

TABLE 16

| PEG in Medium, % | Initial Osmolality, mM/kg[(1)] | Osmolality after Dilution, mM/kg | Embryo Yield | Embryo Quality | Final Osmolality, mM/kg |
| --- | --- | --- | --- | --- | --- |
| 15.0 | 315 | — | 50+ | Note 1 | — |
| 17.5 | 372 | — | 50+ | Note 1 | — |
| 20.0 | 465 | — | 100+ | Note 1 | — |
| 22.5 | 543 | — | 100+ | Note 1 | — |
| 25.0 | 657 | 450 | 100+ | Note 2 | 415 |
| 26.0 | 731 | 490 | 100+ | Note 2 | 505 |
| 27.0 | 798 | 621 | 100+ | Note 2 | 578 |
| 28.0 | 861 | — | 100+ | Note 3 | — |
| 29.0 | 931 | — | 100+ | Note 3 | — |
| 30.0 | 1011 | — | 200+ | Note 3 | — |

Figure 9:
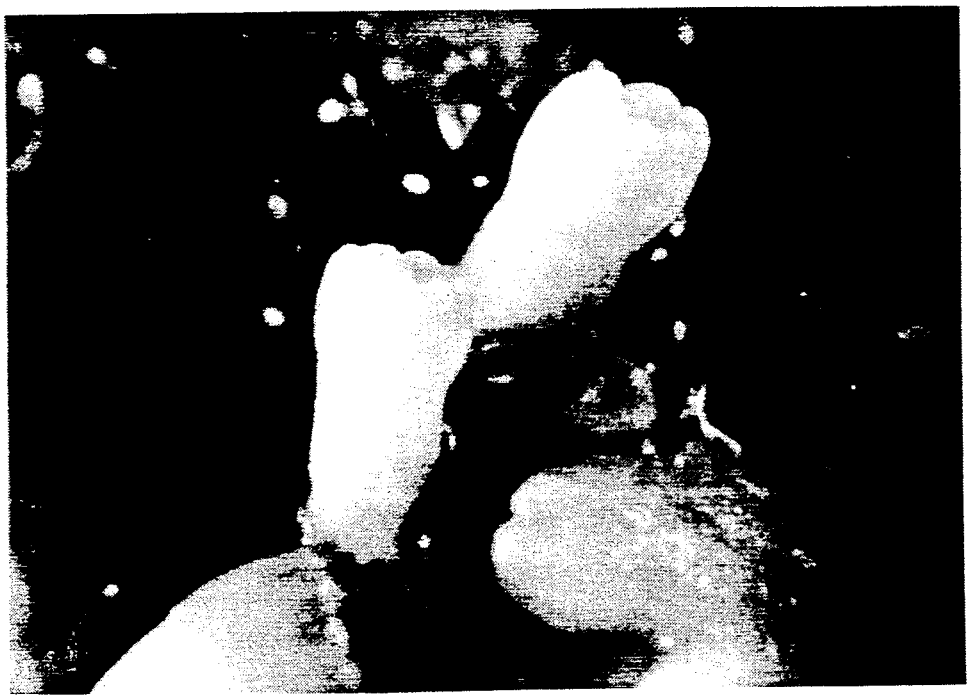
FIG. 9 is a photomicrograph of high quality Douglas-fir cotyledonary embryos.

[(1)]Measured before transfer of cells.
Note 1. Embryos were slightly green and small with swollen hypocotyls.
Note 2. Best quality embryos, yellow in color and with well developed cotyledons. An elongated hypocotyl region similar to zygotic embryos.
Note 3. Good quality embryos but about half the size of embryos produced in 25-27% PEG Embryos produced using 25–27% polyethylene glycol are shown in the photomicrograph of FIG. 9. These have a close resemblance to zygotic embryos and have a high rate of germination and conversion to plants.

In some instances there has been evidence of nutrient exhaustion when the pad system is used with liquid medium. This has been overcome by using a pad-on-pad culture which effectively doubles the amount of medium present.

EXAMPLE 11

A series of experiments was made to compare the effectiveness of solid development media containing various ternary combinations of polyethylene glycol 8000, sorbitol, and lactose all having a similar osmolality of about 450 mM/kg. These were compared with a control medium having only sorbitol and with another having sorbitol and polyethylene glycol 8000. Stage 5 medium (see Tables 10 and 11) was used with 2500 mg/L KNO$_3$, 750 mg/L L-glutamine, 30 mg/L initial abscisic acid, and 0.125% Sigma activated charcoal. The osmoticants, in addition to the 2% sucrose in the basal medium, were as follows.

TABLE 17

| Medium No. | Sorbitol, % | PEG, % | Lactose, % | Osmolality, mM/kg | Osmolar Ratio S:P:L |
| --- | --- | --- | --- | --- | --- |
| 4656 | 3.0 | 0.0 | 0.0 | 386 | 1:0:0 |
| 4982 | 3.5 | 6.0 | 0.0 | 439 | 7:1:0 |
| 4984 | 2.0 | 11.0 | 0.0 | 422 | 1:1:0 |
| 4983 | 3.0 | 6.0 | 1.0 | 438 | 6:1:1 |
| 4985 | 2.0 | 8.0 | 2.0 | 445 | 2:1:1 |
| 4986 | 1.25 | 10.0 | 2.5 | 458 | 3:3:3 |
| 4987 | 0.0 | 12.0 | 4.0 | 447 | 0:1:1 |

The media were made by combining all ingredients except abscisic acid and heat sterilizing. The temperature was reduced to about 60°–65° C. and filter sterilized ABA was added with stirring for 10 minutes before plates were poured and cooled. Medium 4984 gelled somewhat prematurely but produced useable plates. About 24 hours later 1 mL of settled cells (from Stage 4) of five genotypes was plated onto the test media. After four weeks the cultures were examined and cotyledonary embryos counted and graded. The following average numbers of well developed embryos per plate were obtained. One genotype (703) did not produce embryos in any of the media tested here.

TABLE 18

| Medium No. | Genotype 735 | Genotype 711 | Genotype 742 | Genotype 676 |
| --- | --- | --- | --- | --- |
| 4656 | 9.8 | 0.8 | 5.5 | 4.3 |
| 4982 | 47.0 | 31.5 | 0.3 | 8.0 |
| 4984 | 71.3 | 61.3 | 5.7 | 17.7 |
| 4983 | 36.0 | 74.3 | 4.0 | 17.3 |
| 4985 | 100.0 | 143.3 | 27.3 | 9.0 |
| 4986 | 136.0 | 162.8 | 1.3 | 10.3 |
| 4987 | 125.0 | 91.3 | 21.0 | 18.3 |

It is evident that the best results were obtained from media 4985, 4986 and 4987 which were either ternary combinations or binary combinations of polyethylene glycol 8000 and lactose without any sorbitol. The effect of medium composition on performance of individual genotypes appears most markedly with Genotype 742. However, the trial on Medium No. 4986 should be replicated with this genotype before firm conclusions as to its performance are drawn.

EXAMPLE 12

After long periods of time on a development medium containing polyethylene glycol Douglas-fir embryos often show signs of deterioration over time. It has not been clear whether this deterioration was due to nutrient depletion, a decrease in osmotic levels, or a negative response to PEG. The following study was made in order to determine the effect on this deterioration by making a medium and osmoticant change during development. Cultures were made using the liquid medium-polyester pad system described in Example 10.

A development medium was made using 2500 mg/L KNO$_3$, 750 mg/L L-glutamine, 260 g/L polyethylene glycol 8000, and 0.1% activated charcoal. No abscisic acid was included in the medium. The polyester pads were dipped into this medium, as described in Example 10, and picked up about 5.5 g of the medium.

A rinse medium was made in similar fashion to the above with the exception that the PEG and charcoal were omitted and 2.5 ppm of ABA was included. Embryos and associated cells from the final singulation medium were settled and the supernatant liquid removed. One volume of the rinse medium was added and mixed well. The cells and embryos were again settled and half of the supernatant liquid was removed. The embryos and remaining liquid were again mixed and 1.5 mL was pipetted onto the pads. Five genotypes were used with four replicates per treatment.

Osmotic level of the medium over the cells after the rinse was about 200 mM/kg whereas the development medium before plating the cells was about 490 mM/kg. Duplicate osmolality readings were taken from the media on the pads at 3 and 4 weeks after the initial plating.

To attempt to find an answer to the questions posed above, after three weeks 2.0 mL of the original development medium, now diluted with the transferred rinse medium, was pipetted from three groups of plates (5 genotypes×4 replicates×3 sets) and replaced with an equivalent amount of fresh medium made up as follows. The original medium was kept on one set (Set 1) (5 genotypes×4 replicates) as a control.

None of the replacement media contained activated charcoal. Sufficient charcoal remained with the original media still on the pads.

Set 2 Replacement Medium—Original 260 g/L PEG replaced with 221 g/L PEG. Osmolality 512 mM/kg.

Set 3 Replacement Medium—Original 260 g/L PEG replaced with 61 g/L sorbitol. Osmolality 502 mM/kg.

Set 4 Replacement Medium—Original 260 g/l PEG replaced with 120 g/L lactose. Osmolality 516 mM/kg.

TABLE 19

| Genotype | Osmolality, 3 Weeks After Initial plating, mM/kg |
|---|---|
| 735 | 401 |
| 711 | 430 |
| 742 | 632 |
| 703 | 510 |
| 676 | 389 |

TABLE 20

| | Somatic Embryos Developed for Different Genotypes[1] | | | | |
|---|---|---|---|---|---|
| Set No. | 735 | 711 | 742 | 703 | 676 |
| 1 | 87 | 101 | 17 | 32 | 0 |
| 2 | 148 | 118 | 18 | 84 | 1 |
| 3 | 164 | 148 | 11 | 104 | 0 |
| 4 | 202 | 130 | 26 | 126 | 0 |

[1]Average of 4 plates counted 12 days after medium replacement.

Quality was evaluated as follows:

Set 1—Small and declining embryos.

Set 2—Somewhat larger and better appearing embryos.

Set 3—Large, smoother embryos.

Set 4—Largest, smoothest, and best appearing embryos.

While this test is still in progress, it appears that replacement of PEG with lactose or sorbitol midway during development will be advantageous. Osmolality has not yet been measured after the replacement medium was added but is expected to be in the range of 450 mM/kg or above at the end of the development period.

EXAMPLE 13

It appears possible to develop Douglas-fir embryos without any exogenous abscisic acid in the development medium environment. Good quality embryos have been formed even when no ABA was added to the medium during makeup and little or none carried along with the embryos and associated cells from the singulation step. However, a small amount of activated charcoal; e.g., 0.02%, appears to be essential. This may be due to a high level of endogenous ABA within the embryos at the end of singulation, although analytical work has not yet been done to confirm this. In the following experiment three solid media were made up. Each had 1000 mg/L of L-glutamine, 2500 mg/L of $KNO_3$, and 150 g/L of polyethylene glycol 8000.

TABLE 21

| | Medium No. | | |
|---|---|---|---|
| | 1 | 2 | 3 |
| Activated charcoal, % | 0.02 | 0.04 | 0.04 |
| Abscisic acid, mg/L | — | 8 | 8 |
| Sorbitol, % | 2 | 2 | — |

Three genotypes (711, 735, 771) of Douglas-for singulated embryos were used in the trials. These were not washed but 1.5 mL was transferred in the singulation medium to the culture plates. A low level of ABA would have been present at the end of singulation. Five replicates were made at each test condition. After four weeks over 100 embryos had formed on each medium for each genotype. After five weeks the embryos formed on the medium without ABA showed some elongation indicative of premature germination. This was not observed for the embryos formed on the media containing ABA.

It would appear that an osmotic level above about 450 mM/kg may be a threshold value for Douglas-fir embryo development media if the best yield and quality are to be obtained. This level is one measured at the end of the development period rather than the beginning. Ideally, it is believed advantageous for the osmotic level to rise somewhat over the period of development. It is possible to control osmotic level during development by periodic medium changes. To facilitate this without disturbance to the developing embryos they may be supported on a material such as filter paper which is placed directly on either a solid culture medium or on the saturated pad of a liquid medium.

Similarly, it appears important to have a level of available exogenous abscisic acid that drops essentially continuously from the initial usage at the beginning of the singulation stage to the end of the development period. An initial level at the beginning of singulation of about 5-15 ppm appears suitable. This will decrease to a low level at the end of the development stage. Exact measurements have not been possible at the end of development due to the limitations of available analytical techniques.

Following embryo development the somatic embryos may be retained for some period of time in cold storage. They may be converted into artificial seeds for field or nursery planting. Alternatively, they may be placed immediately on a germination medium such as Medium BM$_G$ (Table 10) for conversion into plantlets prior to planting in soil.

Figure 10:
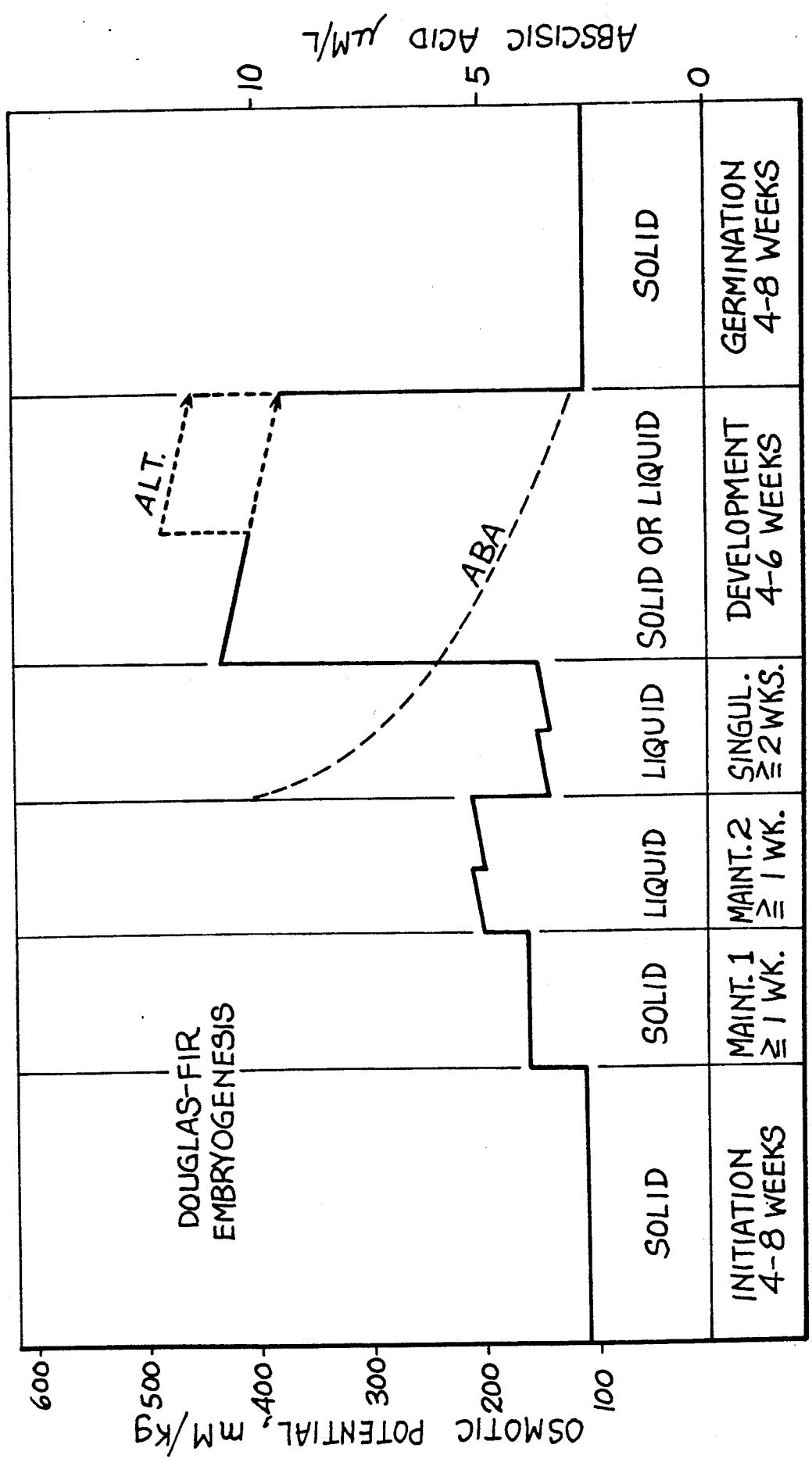
FIG. 10 is a graph showing typical levels of osmotic potential and abscisic acid concentration during the culture of Douglas-fir.

FIG. 10 contains somewhat idealized curves for Douglas-fir showing the osmotic levels and abscisic acid level at each of the various stages from initiation through germination. It has been observed that the osmotic level will increase somewhat during each liquid shake stage of late proembryo development and singulation. The opposite phenomenon seems to occur during development, probably due to utilization of sucrose and other nutrients. Taking this drop into account is necessary in adjusting the initial osmotic level of the development media. Here the solid portion of the curve represents the normal course of osmotic level if no media changes are made. The dotted portion shows how osmotic level can be increased if one or more transfers to fresh media are made.

To date 446 converted seedlings from 13 genotypes of Douglas-fir are growing in soil.

It should be recognized that there is not one single set of culturing conditions that will be suitable for achieving somatic embryogenesis of all species or for all genotypes within a species. Tissue culture as a whole is a highly unpredictable science. This statement has even greater applicability to somatic embryogenesis. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the art of tissue culture. The important discovery of the present invention is the use of a combination of abscisic acid and an adsorbent such as activated charcoal during the growth of late stage proembryos to cotyledonary embryos. This has given results that are far superior in terms of success and consistency than any process reported heretofore. The process has been successfully applied to all of the several species and many genotypes of coniferous plants studied to date and appears to be of general use for all coniferous species.

It will be understood that many variations can be made in the procedures described for the various culturing stages while still remaining within the spirit of the present invention. It is the intention of the inventors that such variations should be included within the scope of their invention if found defined within the following claims.

BIBLIOGRAPHY

Abo El-Nil, Mostafa, 1980 Embryogenesis of gymnosperm forest trees. U.S. Pat. No. 4,217,730.

Becwar, M. R. and R. P. Feirer, 1989 Factors regulating loblolly pine *Pinus taeda* L.) somatic embryo development. *Institute of Paper Chemistry Report*, Southern Forest Tree Improvement Conference, Raleigh, N.C., June 1989.

Becwar, M. R., T. L. Noland, and S. R. Wann, 1987 A method for quantification of the level of somatic embryogenesis among Norway spruce callus lines. *Plant Cell Reports* 6: 35-38.

Becwar, M. R., S. R. Wann, and R. Nagmani, 1988 A survey of initiation frequency of embryogenic callus among ten families of *Pinus taeda* (loblolly pine). *Abstracts*, 4th International Conifer Tissue Culture Work Group, Aug. 8-12, 1988, Saskatoon, Saskatchewan, Canada.

Boulay, M. P., P. K. Gupta, P. Krogstrup, and D. J. Durzan, 1988 Development of somatic embryos from cell suspension cultures of Norway spruce (*Picea abies* Karst.). *Plant Cell Reports* 7: 134-137.

Bourgkard, F. and J. M. Favre, 1988 Somatic embryos from callus of *Sequoia sempervirens*. *Plant Cell Reports* 7: 445-448.

Buchheim, Julie A., Susan M. Colburn, and Jerome P. Ranch, 1989 Maturation of soybean somatic embryos and the transition to plantlet growth. *Plant Physiology* 89: 768-775.

Durzan, D. J. and P. K. Gupta, 1987 Somatic embryogenesis and polyembroyogenesis in Douglas-fir cell suspension cultures. *Plant Science* 52: 229-235.

Finer, John J., Howard B. Kriebel, and Michael R. Becwar, 1989 Initiation of embryogenic callus and suspension cultures of eastern white pine (*Pinus strobus* L.). *Plant Cell Reports* 8: 203-206.

Gupta, Pramod K. and Don J. Durzan
  1985 Shoot multiplication from mature trees of Douglas-fir (*Pseudotsuga menziesii*) and sugar pine (*Pinus lambertiana*). *Plant Cell Reports* 4: 177-179.
  1986a Somatic polyembryogenesis from callus of mature sugar pine embryos. *Bio/Technology* 4: 643-645.
  1986b Plantlet regeneration via somatic embryogenesis from subcultured callus of mature embryos of *Picea abies* (Norway spruce). *In Vitro Cellular and Developmental Biology* 22: 685-688.
  1987 Biotechnology of somatic polyembryogenesis and plantlet regeneration in loblolly pine. *Bio/Technology* 5: 147-151.

Hakman, Inger and Sara von Arnold
  1985 Plantlet regeneration through somatic embryogenesis in *Picea abies* (Norway spruce). *Journal of Plant Physiology* 121: 149-158.
  1988 Somatic embryogenesis and plant regeneration from suspension cultures of *Picea glauca* (White spruce). *Physiologia Plantarum* 72: 579-587.

Hakman, Inger, Larry C. Fowke, Sara von Arnold, and Tage Eriksson, 1985 The development of somatic embryos in tissue cultures initiated from immature embryos of *Picea abies* (Norway spruce). *Plant Science* 38: 33-35.

Johansson, Lars, 1983 Effects of activated charcoal in anther cultures. *Physiologia Plantarum* 59: 397-403.

Johansson, Lars, Barbro Andersson, and Tage Eriksson, 1982 Improvement of anther culture technique: activated charcoal bound in agar medium in combination with liquid medium and elevated $CO_2$ concentration. *Physiologia Plantarum* 54: 24-30.

Lu, Chin-Yi, and Trevor A. Thorpe, 1987 Somatic embryogenesis and plantlet regeneration in cultured immature embryos of *Picea glauca*. *Journal of Plant Physiology* 128: 297-302.

Murashige, Toshio and Folke Skoog, 1962 A revised medium for rapid growth and bioassays with tobacco tissue cultures. *Physiologia Plantarum* 15: 473-493.

Nagmani, R. and J. M. Bonga, 1985 Embryogenesis in subcultured callus of *Larix decidua*. *Canadian Journal of Forest Research* 15: 1088-1091.

Nagmani, R. and M. R. Becwar, 1988 Factors affecting somatic embryo development in loblolly pine. *Abstracts*, 4th International Conifer Tissue Culture Work Group, Aug. 8-12, 1988, Saskatoon Saskatchewan, Canada.

Raghavan, V. N., 1987 *Experimental Embryogenesis*, p 100, McMillan, New York.

Schuller, Astrid and Gerhard Reuther, 1989 Response of *Abies alba* embryonal-suspensor mass to various carbohydrate treatments. *Somatic Cell Genetics Working Party S2-04-07 and NATO Advanced Research Workshop on Woody Plant Biology*, Institute of Forest genetics, Placerville, Calif., Oct. 15-19, 1989 (Abstract).

Singh, Hardev, 1978 "Embryo" in *Embryology of Gymnosperms*, Chapter 11, Gebruder Borntrager, Berlin.

Teasdale, Robert D., Pamela A. Dawson, and Harold W. Woolhouse, 1986 Mineral nutrient requirements of a loblolly pine. (*Pinus taeda* cell suspension culture. *Plant Physiology* 82:942-945.

Von Arnold, Sara, 1987 Improved efficiency of somatic embryogenesis in mature embryos of *Picea abies* (L.) Karst. *Journal of Plant Physiology* 128: 233-244.

Von Arnold, Sara and Inger Hakman, 1988 Regulation of somatic embryo development in *Picea abies* by abscisic acid (ABA). *Journal of Plant Physiology* 132: 164-169.

Yeung, Edward C. and D. C. W. Brown, 1982 The osmotic environment of developing embryos of *Phaseolus vulgaris. Z. Pfanzenphysiol. Bd.* 106 S.: 149-156.

Ziv, Meira and Geula Gadasi, 1986 Enhanced embryogenesis and plant regeneration from cucumber (*Cucumis sativus* L.) callus by activated charcoal in solid/liquid double-layer cultures. *Plant Science* 47: 115-122.

We claim:

1. A method suitable for further developing tissue culture induced coniferous plant species somatic proembryos into well developed cotyledonary embryos which comprises:

transferring and further culturing the proembryos using a development medium having sufficient amounts of mineral and organic nutrient materials along with a sufficient initial amount of abscisic acid and an adsorbent material to gradually reduce the level of available abscisic acid over time, said medium also having sufficient osmoticants to raise the osmotic potential to at least about 350 mM/kg, so as to enable and promote the development and growth of robust cotyledonary embryos having a high potential for normal germination and plant development.

2. The method of claim 1 which further includes generating the proembryos in an initial induction culture medium having a sufficient level of growth hormones, then transferring the proembryos to a maintenance and multiplication medium having a reduced level of growth hormones and an osmotic level at least as high as the induction medium prior to transferring the proembryos to the cotyledonary embryo development medium.

3. The method of claim 2 which further includes transferring the proembryos from the initiation or maintenance and multiplication media to a culture medium having a sufficient amount of growth hormones and an osmotic potential sufficient to induce late stage proembryo development prior to transferring the proembryos to the cotyledonary embryo development medium.

4. The method of claim 1 in which the adsorbent material in the development medium is selected from the group consisting of activated charcoal, silica gel, activated alumina, poly(vinylpyrrolidone), molecular sieves, and mixtures thereof.

5. The method of claim 1 in which the adsorbent material is activated charcoal.

6. The method of claim 1 in which the osmotic potential of the development medium is controlled by a mixture comprising a readily metabolized carbohydrate energy source and at least one additional osmoticant poorly metabolized by the developing embryos.

7. The method of claim 6 in which the readily metabolized carbohydrate is a sugar selected from the group consisting of sucrose, glucose, fructose, maltose, galactose, and mixtures thereof.

8. The method of claim 6 in which the poorly metabolized osmoticant is selected from the group consisting of sorbitol, lactose, a polyalkylene glycol, and mixtures thereof.

9. The method of claim 6 in which the medium is a solid medium gelled by a bacterially generated heteropolysaccharide material.

10. The method of claim 6 in which the development medium is a liquid medium.

11. The method of claim 9 in which the poorly metabolized osmoticant comprises polyethylene glycol in an amount between 20% and 30%.

12. The method of claim 11 in which the polyethylene glycol is present in an amount of about 25%-27%.

13. The method of claims 1 or 6 in which the embryo culture growing in the development medium is transferred at least once to a fresh development medium containing osmoticants.

14. The method of claim 13 in which the osmotic potential of each successive fresh development medium is raised over that of the preceeding development medium.

15. The method of claims 1 or 6 in which the osmotic potential is maintained above about 400 mM/kg throughout the entire development stage.

16. The method of claim 15 in which the osmotic potential is maintained by providing an initial osmotic level sufficiently raised above 400 mM/kg so that it does not drop below about 400 mM/kg during the development stage.

17. The method of claims 1 or 6 in which the osmotic potential is raised during the development period from a lower initial level to a final level of at least about 400 mM/kg.

18. The method of claim 14 in which the final osmotic level is at least about 450 mM/kg.

19. The method of claim 1 in which the plant is Douglas-fir (Pseudotsuga menziesii (Mirb. Franco) cultured from an explant which comprises the zygotic embryo extracted from an immature seed.

20. The method of claim 19 which includes, prior of transfer of proembryos to the development medium, the further step of transferring the proembryos to a liquid culture medium having a reduced osmotic potential and containing a sufficient amount of exogenous abscisic acid to effect singulation of said proembryos.

21. The method of claim 20 in which the osmotic potential of the singulation medium is below about 150 mM/kg.

22. The method of claim 20 in which the initial abscisic acid level is in the range of about 5-15 ppm.

23. The method of claim 20 in which at least one transfer to fresh medium is made during the singulation step, said fresh medium having a lower concentration of abscisic acid than that initially present in the previous medium, said lower concentration being no greater than about that present in the preceeding medium immediately prior to the transfer.

24. The method of claims 20, 21, 22, or 23 in which the initial available abscisic acid concentration in the development medium is no higher than about that present in the singulation medium immediately prior to transfer into the development medium.

25. The method of claim 24 in which the development medium lacks exogenous abscisic acid entirely and a sufficient amount of abscisic acid is transferred with the embryos as entrained or endogenous abscisic acid from the singulation step.

26. The method of claim 20 in which the concentration of abscisic acid to which the developing embryos are exposed is reduced continuously from the beginning of the singulation period until the end of the development period.

* * * * *